United States Patent
Aburatani et al.

(10) Patent No.: US 9,513,292 B2
(45) Date of Patent: Dec. 6, 2016

(54) METHOD FOR DIAGNOSING CANCER BY DETECTING GPC3

(71) Applicant: Perseus Proteomics Inc., Tokyo (JP)

(72) Inventors: Hiroyuki Aburatani, Tokyo (JP); Yutaka Midorikawa, Tokyo (JP); Kiyotaka Nakano, Shizuoka (JP); Iwao Ohizumi, Shizuoka (JP); Yukio Ito, Tokyo (JP); Susumu Tokita, Tokyo (JP)

(73) Assignee: Perseus Proteomics Inc., Tokyo (JP)

( * ) Notice: Subject to any disclaimer, the term of this patent is extended or adjusted under 35 U.S.C. 154(b) by 44 days.

(21) Appl. No.: 14/579,474

(22) Filed: Dec. 22, 2014

(65) Prior Publication Data

US 2015/0132782 A1 May 14, 2015

Related U.S. Application Data

(62) Division of application No. 10/526,508, filed as application No. PCT/JP03/11320 on Sep. 4, 2003, now abandoned.

(51) Int. Cl.
*G01N 33/574* (2006.01)

(52) U.S. Cl.
CPC .. *G01N 33/57438* (2013.01); *G01N 33/57488* (2013.01); *G01N 33/57492* (2013.01); *G01N 2333/4722* (2013.01); *G01N 2400/00* (2013.01)

(58) Field of Classification Search
CPC ...................................................... G01N 33/574
USPC ............................................... 435/7.23, 7.92
See application file for complete search history.

(56) References Cited

U.S. PATENT DOCUMENTS

| | | | |
|---|---|---|---|
| 5,644,026 A | 7/1997 | Yamaguchi et al. |
| 5,760,000 A | 6/1998 | Habibi |
| 5,807,860 A | 9/1998 | Inoue et al. |
| 5,843,937 A | 12/1998 | Wang et al. |
| 6,268,336 B1 | 7/2001 | Niitsu et al. |
| 6,486,144 B1 | 11/2002 | Morris |
| 7,883,853 B2 | 2/2011 | Filmus et al. |

OTHER PUBLICATIONS

Sakali, Z. et al. "Expression of Glypican 3 (GPC3) in Embryonal Tumors". Int. J. Cancer. Sep. 2000. vol. 89, No. 5 pp. 418-422.
Ushiku et al., "Glypican 3-expressing gastric carcinoma: distinct subgroup unifying hepatoid, clear-cell, and alpha-fetoprotein-producing gastric carcinomas." Cancer Sci, vol. 100, No. 4, pp. 626-632, Apr. 2009.
Yamanaka et al., "Immunohistochemical study of glypican 3 in thyroid cancer.", Oncology; 73: pp. 389-394 (2007).
Okon et al., "Glypican-3 is expressed in chromophobe renal cell carcinomas.", Pol J. Pathol, 59, 1, pp. 15-20 (2008).
Maeda et al., "Glypican-3 expression in clear cell adenocarcinoma of the ovary." Modern Pathology 22, 824-832 (2009).
Aviei-Ronen et al., "Glypican-3 is overexpressed in lung squamous cell carcinoma, but not in adenocarcinoma.", Modern Pathology 21, 817-825 (2008).
Zynger et al., "Expression of glypican 3 in ovarian and extragonadal germ cell tumors.", Am J Clin Pathol; 130: 224-230, (2008).
Taketa et al., "A collaborative study for the evaluation of lectin-reactive alpha-fetoproteins in early detection of hepatocellular carcinoma.", Cancer Research 53, 5419-5423, Nov. 15, 1993.
Chan et al., "Evaluation of a monoclonal immunoenzymometric assay for alpha-fetoprotein.", Clin Chem. 3217, 1318-1322 (1986).
Stephan et al., "Molecular forms of prostate-specific antigen and human kallikrein 2 as promising tools for early diagnosis of prostate cancer.", Cancer Epidemology, Biomarkers and Prevention, vol. 9, 1133-47, Nov. 2000.
Guess et al., "Benign prostatic hyperplasia and prostate cancer.", Epidemiologic Reviews, vol. 23, No. 1, 2001.
Jain et al., "Improving the utility of prostate specific antigen (PSA) in the diagnosis of prostate cancer: the use of PSA derivatives and novel markers.", Postgrad Med J.; 78: 646-650, (2002).
Nilsson et al., "Sensitivity and specificity of CA242 in gastrointestinal cancer. A comparison with CEA, CA50 and CA 19-9.", Br. J. Cancer, 65, 215-221 (1992).
Pasanen et al., "Receiver operating characteristic (ROC) curve analysis of the tumour markers CEA, CA 50 and CA 242 in pancreatic cancer; results from a prospective study.", Br. J. Cancer, 67, 852-855 (1993).
Takada et al., "Measurement of cytokeratin 19 fragments as a marker of lung cancer by CYFRA 21-1 enzyme immunoassay.", British Journal of Cancer 71, 160-65, (1995).
Nisman et al., "Evaluation of urine CYFRA 21-1 for the detection of primary and recurrent bladder carcinoma.", American Cancer Society (2002), vol. 94, No. 11, pp. 2914-2922 (Jun. 1, 2002).
Ding Guanghui et al., "Distribution of GPC 3 Fusion Protein in Hepatocellular Carcinoma (HCC) and its Clinical Significance," Chinese Journal of Anatomy, vol. 24, No. 6, 2001, p. 499-503; English Abstract on p. 502.
Abstract #1097, Capurro et al., "Overexpression of Glypican-3 in human hepatocellular carcinomas determined by immunohistochemistry using a monoclonial antibody," Proceedings of the American Association for Cancer Research, Clinical Research 5, vol. 43, Mar. 2002, p. 219.
Celis, et al., "Gene expression profiling: monitoring transcription and translation products using DNA microarrays and proteomics," FEBS Letters 480 (2000) pp. 2-16.
Anderson, et al., "A comparison of selected mRNA and protein abundances in human liver," Electrophoresis (1997) 18, PD. 533-537.
Liotia, et at.,"Molecular Drofilinq of human cancer," Nature Reviews Genetics, (Oct. 2000} vol. 1, PD. 48-56.

(Continued)

*Primary Examiner* — Yan Xiao
(74) *Attorney, Agent, or Firm* — Davidson, Davidson and Kappel LLC

(57) ABSTRACT

Provided is a method for diagnosing cancer by detecting a novel cancer marker. Cancer can be diagnosed by detecting soluble glypican 3 in a test sample.

5 Claims, 9 Drawing Sheets

(56) References Cited

OTHER PUBLICATIONS

Bertucci, et at., "Gene expression profiling of cancer by use of DNA arrays: how far from the clinic?," The Lancet Oncology, (Nov. 2001) vol. 2, PD. 674-682.
Nelson. Nancy,•Microarrays Pave the Way to 21 "Century Medicine," Journal of the National Cancer Institute, (Dec. 18, 1996), vol. 88, No. 24, pp. 1803-1805.
Hough, et al., "Large-scale serial analysis of gene expression reveals genes differentially expressed in ovarian cancer," Cancer Research 60, (Nov. 15, 2000), pp. 6281-67.
Wei Zhou, et al., "Identifying markers for pancreatic cancer by gene expression analysis," Cancer Epidemiology, (Feb. 1998) vol. 7, pp. 109-112.
Teck Keong Seow, et al., "Hepatocellular carcinoma: from bedside to proteomics," Proteomics (2001), 1, PD. 1249-1263.
Huber. et al., "Tumorigenicity and transcriptional modulation of c-myc and N-ras oncogenes in a human hepatoma cell line," Cancer Research, (Sep. 1985). 45, PD. 4322-4329.
Kraft, et al., "Suramin inhibits growth and yet promotes insulin-like growth factor II expression in HepG2 cells," Cancer Research (Feb. 1, 1993) 53, pp. 652-657.
Castaneda, et al., "Cytotoxicity of millimolar concentrations of ethanol on HepG2 human tumor cell line compared to normal rat hepatocytes in vitro," J Cancer Res Clin Oncol (2000) 126:503-510.
Pati, et al., "Inhibition of human hepatocarcinoma cell proliferation by mammalian and fish gonadotropin-releasing hormones," Endocrinology (1995), vol. 136, No. 1, pp. 75-64.
Knowles, et al., "Human hepatocellular carcinoma cell lines secrete the major plasma proteins and Hepatitis B surface antigen," Science, (Jul. 25, 1980), vol. 209, PD. 497-499.
Zhu Z-W et al: "Enhanced glycipan-3 expression differentiates the majority of hepatocellular carcinomas from benign hepatic disorders" GUT, British Medical Association, London,GB, vol. 48,Oct. 17, 2001 (Oct. 17, 2001),pp. 558-564, XP002959808 ISSN: 0017-5749.
Kleeff J H et al: "Giypican-3 is a potential tumor marker for hepatocellular carcinoma" Gastroenterology, Elsevier, Philadelphia, PA, US, vol. 118,No. 4, Suppl2, Part I , 2000,p. A261,AbstractI501, XP002959809ISSN: 0016-5085.
Nackaerts Ketal: "Heparan Sulfate Proteoglycan Expression in Human Lung-Cancer Cells" International Journal of Cancer,New York, NY, US, vol. 74, 1997,pp. 335-345, XP002925654 ISSN: 0020-7136.
Hey-Chi Hsu et al., Cloning and Expression of a Developmentally Regulated Transcript MXR7 in Hepatocellular Varsinoma: Biological Significance and Temporospatial Distribution, Cancer Research, vol. 57, pp. 5179-5184, Nov. 15, 1997.
Jorge Filmus, Glypicans in Growth Control and Cancer, Glycobiology, vol. 11, No. 3, pp. 19R-23R, 2001.
Ward (Developments in Oncology 1985; 21: 91-106).
Chen et al. (Clinica Chimica Acta, 2013, 423: 105-111).
Nakatsura et al. (Biochemical and Biophysical Research Communications, 2003, Jun. 20, 306: 16-25).
Harlow and Lane (Antibodies, a Laboratory Manual, Cold Spring Harbor Laboratory Press, 1988, p. 141-142).
Capurro et al. (Gastroenterology Jul. 2003 125:89-97).
Powell et al. (Chest 2002 121: 6s-7s).
Zhu et al. (Amer. J. Surgery 2002 184: 78-83).
Busken, C et al, (Digestive Disease Week Abstracts and Itinerary Planner, 2003, abstract No. 850).
Kaiser (Science, 2006, 313:1370).
Pilia et al. (Nature Genetics, Mar. 1996, 12:241-247.
Harlow and Lane (Antibodies, a Laboratory Manual, Cold Spring Harbor Laboratory Press, 1988, p. 591, hereafter Harlow and Lane).
Drexler et al, 1993 (Leukemia and Lymphoma, 9:1-25).
Tian, Jet al, 2004 (Physiol Genomics, 17: 170-182).
Van Dyke D L et al, 2003 (Cancer Genetics and Cytogenetics 241: 137-141).
Kunkel, P, et al, 2001 (Neuro-oncology 3(2): 82-88).
Schmid Setal, 2001 (J comparative Neurology, 430(2): 160-71).
Conner et al, 1996 (Mol Brain Res, 42: 1-17).
Brennan et al (Journal of Autoimmunity, 1989, vol. 2 suppl., pp. 177-186).
Zimmer (Cell Motility and the Cytoskeleton, 1991, vol. 20, pp. 325-337).
Eriksson et al. (Diabetologia, 1992. vol. 35, pp. 143-147).
Freshney (Culture of Animal Cells, A Manualof Basic Technique, Alan R. Liss. Inc., 1983, New York, p. 4).
Dermer (Bio/Technology, 1994, 12:320).
Hippo et al. (2004, Cancer Research 64:2418-2423).
(Nakatsura et al., 2005, Biodrugs 19(2):71-77).

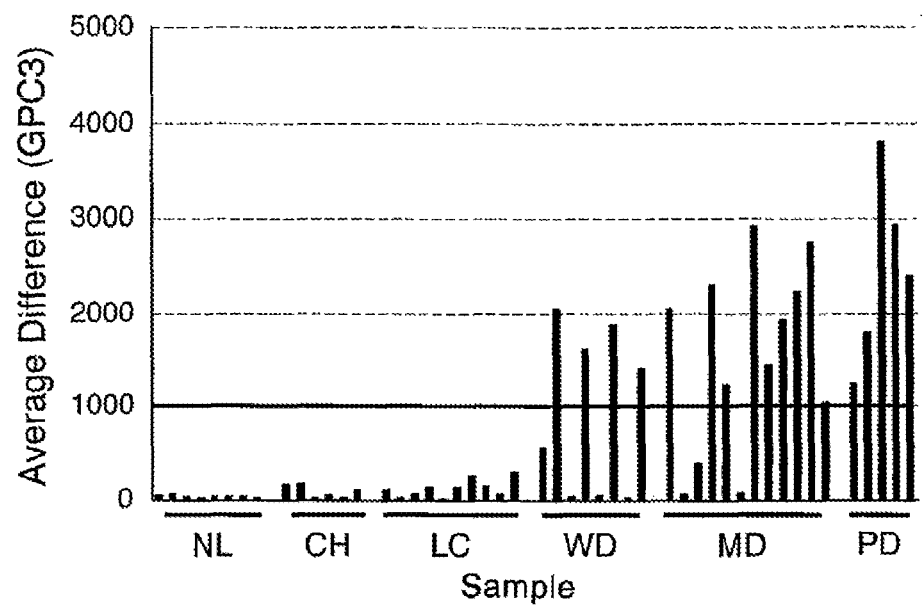
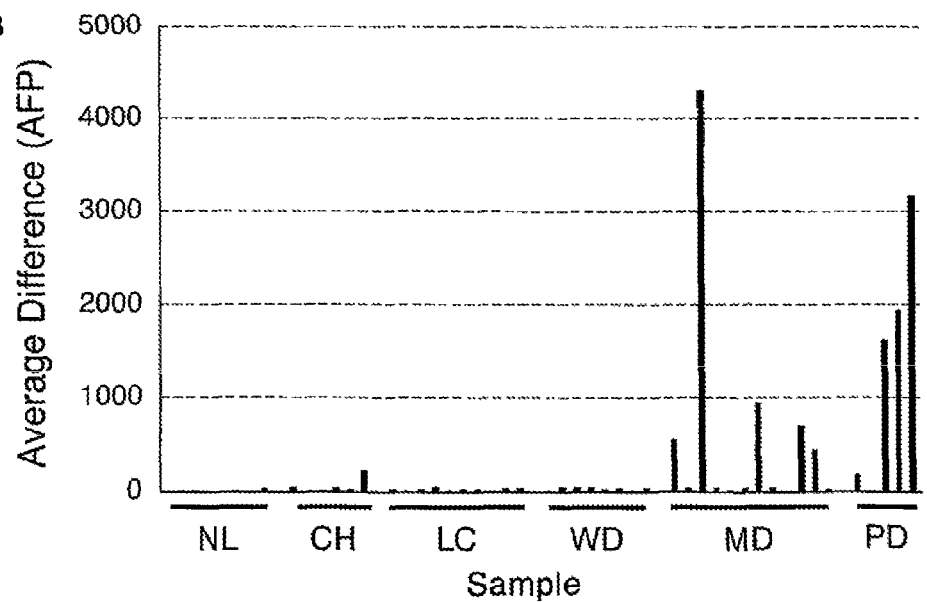

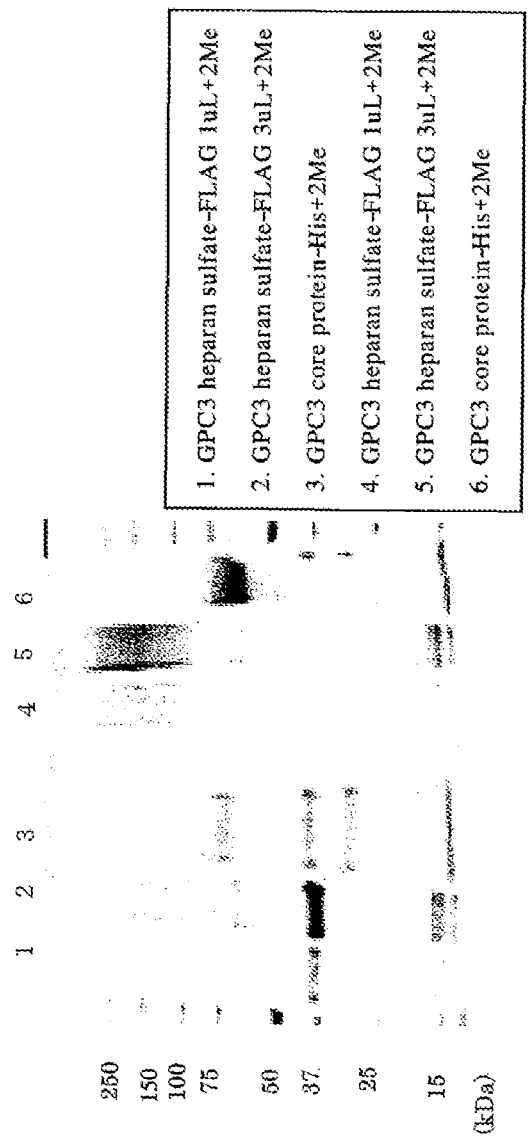

Fig. 8

|  | Form of soluble GPC3 | | |
|---|---|---|---|
|  | N-terminus only | N+C | C-terminus only |
| N-N ELISA | + | + | − |
| N-C ELISA | − | + | − |
| C-C ELISA | − | + | + |

METHOD FOR DIAGNOSING CANCER BY DETECTING GPC3

This application is a divisional application of U.S. application Ser. No. 10/526,508, filed on Mar. 4, 2005, which is a national phase application under 35 U.S.C. §371 of International Application No. PCT/JP02/08997, filed in Japan on Sep. 4, 2002, through International Application No. PCT/JP2003/011320, filed Sep. 4, 2003.

FIELD OF THE INVENTION

The pre sent invention relates to a soluble cancer marker in blood, and specifically relates to a method for diagnosing cancer by detecting soluble glypican 3 (GPC3) in a clinical sample.

BACKGROUND OF THE INVENTION

The glypican family has been reported to be present as a new family of heparan sulfate proteoglycans that are present on cell surfaces. To date, the 5 types of glypicans (glypican 1, glypican 2, glypican 3, glypican 4 and glypican 5) have been reported as members of the glypican family. These members of the family have a core protein of uniform size (approximately 60 kDa), share specific and well-conserved cysteine sequences, and bind to cell membranes via glycosyl phosphatidyl inositol (GPI) anchors.

Glypican 3 (GPC3) has been known to be involved in cell division, or the control of cell division pattern during development, and that a GPC3 gene is highly expressed in hepatic cancer cells. Accordingly, the GPC3 gene may be used as a hepatoma marker.

We have previously found that an anti-GPC3 antibody has ADCC activity and CDC activity, and is useful for the therapy of hepatic cancer, and have applied for a patent (Japanese Patent Application No. 2001-189443).

GPC3 is a membrane-bound protein. It has not been reported that a secretory type GPC3 is present in blood and that the GPC3 protein can be used as a cancer marker.

SUMMARY OF THE INVENTION

We have discovered that glypican 3 (GPC3) is cleaved between the 358th arginine and the 359th serine, and thus hypothesized that a soluble GPC3 is secreted in blood of hepatic cancer patients. We then established a sandwich ELISA system of GPC3, and revealed the presence of GPC3 protein in the culture supernatant of HepG2 (human hepatic cancer cells) that highly express GPC3 gene. Furthermore, we also succeeded in measuring a soluble GPC3 not only in the plasma of a mouse grafted with HepG2, but also in the sera of human hepatic cancer patients. Since the gene expression of GPC3 in hepatic cancer is observed at an earlier stage than that of AFP, which is a cancer marker, it has been considered that the detection of GPC3 protein is useful for the diagnosis of cancer. Furthermore, the detection of soluble GPC3 is somewhat difficult by using anti-GPC3 antibodies that can recognize the C-terminal fragment. It has been inferred that the secretory GPC3 protein dominantly comprises the N-terminal fragment. Therefore, we speculated that anti-GPC3 antibodies that recognize the N-terminus can be used to detect soluble GPC3, thereby completing the present invention.

The expression of GPC3 protein has also been detected in cancer cell lines other than hepatic cancer cell lines, such as lung cancer, colon cancer, mammary cancer, prostate cancer, pancreatic cancer, and lymphomas. Hence, GPC3 may possibly be applied to the diagnosis of hepatic cancer as well as many other cancers.

The present invention is as follows.

(1) A method for diagnosing cancer, which comprises detecting a soluble GPC3 protein in a test sample.
(2) The method for diagnosing cancer of (1), wherein the soluble GPC3 protein is a N-terminal peptide of GPC3.
(3) The method for diagnosing cancer of (2), wherein the N-terminal peptide of GPC3 is a peptide fragment contained in an amino acid sequence of GPC3 consisting of the 1st amino acid to the 374th amino acid, or an amino acid sequence of GPC3 consisting of the 1st amino acid to the 358th amino acid.
(4) The diagnosis method of any one of (1) to (3), wherein the test sample is selected from the group consisting of blood, serum and plasma.
(5) The diagnosis method of any one of (1) to (4), wherein the cancer is hepatic cancer.
(6) The method of any one of (1) to (5), comprising using an anti-GPC3 antibody.
(7) The method of (6), comprising using an anti-GPC3 antibody immobilized on a carrier and an anti-GPC3 antibody labeled with a labeling substances.
(8) The method of (7), wherein the labeling substances are biotin.
(9) A diagnostic reagent for cancer, comprising an anti-GPC3 antibody.
(10) The diagnostic reagent of (9), comprising an anti-GPC3 antibody immobilized on a carrier and an antibody labeled with a labeling substance.
(11) The diagnostic reagent of (9) or (10), wherein the cancer is hepatic cancer.
(12) The diagnostic reagent of anyone of (9) to (11), wherein the anti-GPC3 antibody recognizes the N-terminal peptide of GPC3.
(13) A diagnostic kit, comprising an anti-GPC3 antibody, and
(14) The diagnostic kit of (13), comprising the anti-GPC3 antibody immobilized on carriers, and an antibody labeled with a labeling substance.

The present invention will be described in detail as follows.

The present invention relates to a method for detecting cancer by detecting soluble glypican in a test sample.

The meaning of "detection" includes quantitative detection and qualitative detection. Examples of qualitative detection include measurement to simply determine whether or not GPC3 proteins are present, measurement to determine whether or not the content of GPC3 proteins are greater than the basal level, and measurement to compare the level of GPC3 proteins in a test sample with that of another sample (e.g., a control sample). Examples of quantitative detection include measurement of the concentration of GPC3 proteins and measurement of the level of GPC3 proteins.

The test sample includes any samples that may contain GPC3 proteins. The test sample is preferably collected from the body of an organism such as a mammal, and further preferably collected from a human. Specific examples of the test sample include blood, intercellular fluid, plasma, extravascular fluid, cerebrospinal fluid, synovial fluid, pleural fluid, serum, lymph, saliva and urine. Preferred test samples are blood, serum and plasma. The test sample of the present invention also includes those derived from a test sample, for example, culture media of cells collected from the body of an organism.

Cancers to be diagnosed according to the invention include, but is not limited to, hepatic cancer, pancreatic cancer, lung cancer, colon cancer, mammary cancer, prostate cancer, leukemia and lymphomas, preferably hepatic cancer.

1. Preparation of Anti-GPC3 Antibodies

The anti-GPC3 antibody used in the present invention may be derived from any origin, and may be of any type (monoclonal or polyclonal) and in any form, as long as it specifically binds to the GPC3 protein. Specifically, known antibodies such as mouse antibodies, rat antibodies, human antibodies, chimeric antibodies or humanized antibodies can be used.

The antibody may be a polyclonal antibody, but preferably a monoclonal antibody.

Furthermore, anti-GPC3 antibodies to be immobilized on carriers and anti-GPC3 antibodies to be labeled with labeling substances may recognize the same epitope on the GPC3 molecule, but preferably recognize different epitopes.

Preferably, epitopes to be recognized by the antibody is present on the N-terminal fragments (from the 1st amino acid Met to the 358th Arg, or the 1st Met to the 374th Lys) of the GPC3 protein.

The anti-GPC3 antibody used in the present invention can be obtained as a polyclonal or monoclonal antibody using known techniques. In particular, as the anti-GPC3 antibody, a monoclonal antibody derived from a mammal is preferably used in the present invention. Examples of the monoclonal antibody derived from a mammal include an antibody produced by a hybridoma and an antibody produced by a host transformed by genetic engineering techniques with an expression vector containing the antibody gene.

A monoclonal antibody-producing hybridoma can be prepared essentially using known techniques as follows. A hybridoma can be prepared by immunizing an animal with GPC3 as an immunogen according to a standard immunization method to obtain immunocytes, which are then fused to known parent cells by a standard cell fusion method. The fused cells are screened for monoclonal antibody-producing cells by a standard screening method.

Specifically, monoclonal antibodies can be prepared as follows.

GPC3 to be used as an immunogen for raising antibodies is first obtained by expressing the GPC3 (MXR7) gene as disclosed by Lage, H. et al (Gene 188 (1997), 151-156). Specifically, the gene sequence encoding GPC3 is inserted in a known expression vector system, an appropriate host cell is transformed, and then the intended human GPC3 protein is purified by a known method from the host cells or the culture supernatant.

In addition, naturally occurred GPC3 can also be purified and used.

Next, the purified GPC3 protein is used as an immunogen. Alternatively, a partial peptide of GPC3 can be used as an immunogen. In this case, the partial peptide can be obtained by chemical synthesis based on the amino acid sequence of human GPC3; incorporation of a part of a GPC3 gene into an expression vector; or degradation of native GPC3 with a proteolytic enzyme. The region of GPC3 to be used as the partial peptide is not limited to any specific regions. To obtain an antibody that recognizes an epitope present on the N-terminal fragment, a peptide ranging from the 1st amino acid Met to the 358th Arg or a peptide ranging from the 1st Met to the 374th Lys of GPC3 may be used. A peptide that contains an epitope of this region but is smaller than the above peptides can also be used.

A mammal to be immunized with an immunogen is not specifically limited, and is preferably selected in consideration of compatibility with a partner cell to be used for cell fusion. For example, rodents such as mice, rats, hamsters or rabbits, or monkeys are generally used.

Animals are immunized with an immunogen according to a known method. For example, immunization is performed by injecting a mammal intraperitoneally or subcutaneously with an immunogen. Specifically, the immunogen is diluted with or suspended in an appropriate volume of PBS (Phosphate-Buffered Saline), physiological saline or the like; mixed with an appropriate volume of a standard adjuvant such as a Freund's complete adjuvant if necessary; emulsified; and then administered to mammals several times every 4 to 21 days. In addition, an appropriate carrier can also be used upon immunization with an immunogen. Particularly when a peptide fragment with a small molecular weight is used as an immunogen, the peptide is preferably bound to a carrier protein such as albumin or Keyhole limpet hemocyanin, and then used for immunization.

Mammals immunized as described above is tested for an increased titer of a desired antibody in the serum. Subsequently, immunocytes are collected from the mammals, and then subjected to cell fusion. A particularly preferred immunocyte is a splenocyte.

A mammalian myeloma cell is used as a partner cell to be fused with the above immunocyte. Examples of a myeloma cell line that is preferably used herein include various known cell lines such as P3 (P3x63Ag8.653) (J. Immnol. (1979) 123, 1548-1550), P3x63Ag8U.1 (Current Topics in Microbiology and Immunology (1978) 81, 1-7), NS-1 (Kohler. G. and Milstein, C. Eur. J. Immunol. (1976) 6, 511-519), MPC-11 (Margulies. D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), 5194 (Trowbridge, I. S. J. Exp. Med. (1978) 148, 313-323) and R210 (Galfre, G. et al., Nature (1979) 277, 131-133).

Cell fusion of the above immunocytes with myeloma cells can be essentially performed according to a known method, for example, the method of Köhler and Milstein et al (Köhler. G. and Milstein, C., Methods Enzymol. (1981) 73, 3-46).

More specifically, the above cell fusion is performed in a standard nutrition culture medium in the presence of, for example, a cell-fusion accelerator. A cell-fusion accelerator includes, for example, polyethyleneglycol (PEG), Sendai virus (HVJ) or the like. If desired, an auxiliary such as dimethylsulfoxide can also be added to further enhance the fusion efficiency.

Any ratio of immunocytes to myeloma cells may be set for use herein. For example, it is preferable that the number of immunocytes be 1 to 10 times greater than that of myeloma cells. As a medium to be used for the above cell fusion, for example, RPMI1640 medium or MEM medium which is appropriate for the growth of the above myeloma cell line, or other standard media that are used for this type of cell culture can be used. Moreover, a serum fluid such as fetal calf serum (FCS) can be used in combination therewith.

Cell fusion is performed by thoroughly mixing certain amounts of the above immunocytes and myeloma cells in the above medium, adding PEG (e.g., with an average molecular weight of approximately 1000 to 6000) solution (at a concentration of 30 to 60% (w/v)) pre-heated at approximately 37° C., and then mixing the solution, so as to form fused cells (hybridomas). Subsequently, reagents for cell fusion or the like that is unfavorable for the growth of the hybridomas is removed by adding an appropriate medium successively, removing the supernatant by centrifugation, and repeating these steps.

The thus obtained hybridomas are selected by culturing the hybridomas in a standard selective medium such as HAT medium (a medium containing hypoxanthine, aminopterin and thymidine). Culture in the above HAT medium is continued for a time period sufficient to kill the non-fused cells (other than the desired hybridoma) (typically several days to several weeks). Subsequently, a standard limiting dilution method is conducted, so that hybridomas that produce the intended antibody are screened and monocloned.

Screening and monocloning a hybridoma producing a desired antibody may be performed by a screening method based on a known antigen-antibody reaction. For example, the antigen is bound to a carrier such as polystyrene beads or the like or a commercially available 96-well microtiter plate, and the culture supernatant of the hybridomas is added to the plate to react with the antigen. After the carrier is washed, an enzyme-labeled secondary antibody or the like is added to determine whether or not an antibody reacting with the immunogen is contained in the culture supernatant. Hybridomas producing the intended antibodies can be cloned by the limiting dilution method or the like. Antigens used for immunization may be used in this screening. To obtain antibodies against the N-terminal fragment of GPC3, the N-terminal fragment may be used as an antigen for screening.

In addition to the above method where a hybridoma is obtained by immunizing non-human animals with the antigen, desired human antibodies having binding activity to GPC3 can also be obtained by sensitizing in vitro human lymphocytes with GPC3, and causing the sensitized lymphocytes to be fused to human-derived myeloma cells having a permanent division potential (see Japanese Patent Publication (Kokoku) No. 1-59878 B (1989)). Alternatively, GPC3 antigen can be administered to a transgenic animal having all the repertories of a human antibody gene to obtain anti-GPC3 antibody-producing cells, and then human antibodies against GPC3 may be obtained from immortalized anti-GPC3 antibody-producing cells (see International Patent Publication Nos. WO 94/25585, WO 93/12227, WO 92/03918 and WO 94/02602).

The thus prepared hybridoma producing a monoclonal antibody can be passage-cultured in a standard medium, or can be stored for a long period in liquid nitrogen.

One example of a method employed to obtain monoclonal antibodies from the hybridoma involves culturing the hybridoma according to a standard method and obtaining monoclonal antibodies in the culture supernatant. Another method involves administrating the hybridoma to a compatible mammal and obtaining monoclonal antibodies from its as cites. The former method is suitable to obtain highly purified antibodies, while the latter method is suitable for the mass production of antibodies.

In the present invention, a recombinant monoclonal antibody produced by genetic engineering techniques can also be used as a monoclonal antibody. The recombinant monoclonal antibody is prepared by cloning the antibody gene from the hybridoma, incorporating the gene into an appropriate vector, introducing the vector into a host, and then causing the host to produce the recombinant monoclonal antibody (e.g., see Vandamme, A. M. et al., Eur. J. Biochem. (1990) 192, 767-775, 1990). Specifically, mRNA encoding the variable (V) region of an anti-GPC3 antibody is isolated from a hybridoma producing the anti-GPC3 antibody. Total RNA is isolated by a known method such as a guanidine ultracentrifugal method (Chirgwin, J. M. et al., Biochemistry (1979) 18, 5294-5299) or AGPC method (Chomczynski, Petal., Anal. Biochem. (1987) 162, 156-159). mRNA is then prepared from the total RNA using mRNA Purification Kit (Pharmacia) or the like. In addition, mRNA can also be directly prepared using QuickPrep mRNA Purification Kit (Pharmacia).

cDNA of the antibody V region is synthesized using reverse transcriptase from the thus obtained mRNA. For example, cDNA is synthesized using AMV Reverse Transcriptase First-strand cDNA Synthesis Kit (SEIKAGAKU CORPORATION) or the like. To synthesize and amplify cDNA, for example, 5'-Ampli FINDER RACE Kit (Clontech) and the 5'-RACE method using PCR (Frohman, M. A. et al., Proc. Natl. Acad. Sci. USA (1988) 85, 8998-9002, Belyaysky, A. et al., NucleicAcids Res. (1989) 17, 2919-2932) can be employed.

The desired DNA fragment is purified from the thus obtained PCR product, and then ligated to a vector DNA to prepare a recombinant vector. Then the vector is introduced into *Escherichia coli* or the like, and colonies are selected, thereby preparing a desired recombinant vector. The nucleotide sequence of the DNA fragment is confirmed by a known method, such as a dideoxynucleotide chain termination method.

Once DNA encoding the V region of the anti-GPC3 antibody is obtained, this DNA is incorporated into an expression vector containing DNA encoding a desired constant region (C region) of an antibody.

To produce the anti-GPC3 antibody used in the present invention, the antibody gene is incorporated into an expression vector so that the gene is expressed under the regulation of a gene expression control region, for example, an enhancer and a promoter. Next, a host cell is transformed with the expression vector, allowing the host cells to express the antibody.

An antibody gene can be expressed by incorporating DNA encoding the antibody heavy chain (H-chain) or DNA encoding the antibody light chain (L-chain) separately into expression vectors, and then simultaneously transforming a host cell with the vectors; or by incorporating DNAs encoding the H-chain and the L-chain into a single expression vector, and then transforming a host cell with the vector (see WO 94/11523).

In addition to the above host cells, a transgenic animal can also be used to produce a recombinant antibody. For example, the antibody gene is inserted in a gene encoding a protein (e.g., goat β casein) uniquely produced in milk to prepare a fused gene. A DNA fragment containing the fused gene comprising the antibody gene is injected into a goat embryo, and then such embryo is introduced into a female goat. Desired antibodies can be obtained from the milk produced by the transgenic goat that has accepted the embryo or its progeny. To increase the milk volume containing the desired antibody produced by the transgenic goat, hormones can be administered to the transgenic goat as necessary (Ebert, K. M. et al., Bio/Technology (1994) 12, 699-702).

In the present invention, in addition to the above described antibodies, artificially altered recombinant antibodies such as chimeric antibodies or humanized antibodies can be used. These altered antibodies can be produced using a known method.

Chimeric antibodies can be obtained by ligating the DNA encoding the above antibody V-region to DNA encoding a human antibody C-region, incorporating the product into an expression vector, and then introducing the vector into a host to cause the host to produce the antibodies. Using this known method, chimeric antibodies useful in the present invention can be obtained.

Humanized antibodies are also referred to as reshaped human antibodies, which are prepared by grafting an antibody CDR (complementarity determining region) of a mammal other than a human, such as a mouse, to the CDR of a human antibody. General gene recombination techniques are known in the art (see European Patent Application Publication No. EP 125023 and WO 96/02576).

Specifically, the DNA sequence that has been designed to ligate a mouse antibody CDR to the framework region (FR) of a human antibody is synthesized by the PCR method using as primers several oligonucleotides that have been prepared to have a portion overlapping the terminal regions of both mouse antibody CDR and the framework region (FR) of a human antibody (see the method as described in WO 98/13388).

The framework region of a human antibody to be ligated via CDR is selected such that the CDR will forma good antigen binding site. Amino acids in the framework region in the antibody variable region may be substituted as required, so that the CDR of a reshaped human antibody forms an appropriate antigen-binding site (Sato, K. et al., Cancer Res. (1993) 53, 851-856).

C regions derived from a human antibody are used for the C regions of a chimeric antibody and a humanized antibody. For example, for the H-chain, Cγ1, Cγ2, Cγ3 or Cγ4C, and for the L-chain, Cκ or Cλ can be used, respectively. In addition, to improve the stability of antibodies or the production process thereof, the human antibody C-region may be modified.

A chimeric antibody consists of the variable region of an antibody derived from a mammal other than a human, and a constant region derived from a human antibody, while a humanized antibody consists of the CDR of an antibody derived from a mammal other than a human, and the framework region and C region derived from a human antibody. Since the antigenicity of the humanized antibody is expected to be reduced in a human body, it is useful as an active component of a therapeutic agent of the present invention.

The antibody used in the present invention is not limited to the entire antigen molecule, but includes a fragment of the antibody or the modified product thereof, as long as it binds to GPC3. Both a bivalent antibody and a monovalent antibody are included. Examples of the fragment of an antibody include Fab, F(ab')2, Fv, Fab/c having one Fab and a complete Fc, and a single chain Fv (scFv) wherein the Fv of the H-chain and the L-chain are linked via an appropriate linker. Specifically, an antibody fragment may be prepared by treating the antibody with an enzyme such as papain or pepsin, or by a method wherein genes encoding these antibody fragments are constructed, introduced into expression vectors, and then expressed in appropriate host cells (see e.g., Co., M. S. et al., J. Immunol. (1994) 152, 2968-2976, Better, M. & Horwitz, A. H. Methods in Enzymology (1989) 178, 476-496, Academic Press, Inc., Plueckthun, A. & Skerra, A. Methods in Enzymology (1989) 178, 476-496, Academic Press, Inc., Lamoyi, E., Methods in Enzymology (1989) 121, 652-663, Rousseaux, J. et al., Methods in Enzymology (1989) 121, 663-669, and Bird, R. E. et al., TIBTECH (1991) 9, 132-137).

scFv is obtained by linking the H-chain V-region and the L-chain V-region of antibodies. In the scFv, the H-chain V-region and the L-chain V-region are linked via a linker, preferably a peptide linker (Huston, J. S. et al., Proc. Natl. Acad. Sci. U.S.A. (1988) 85, 5879-5883). The H-chain V-region and the L-chain V-region in scFv may be derived from any of the antibodies described in this specification. As a peptide linker to link the V-regions, for example, any single-stranded peptide comprising 12 to 19 amino acid residues may be used.

DNA encoding scFv can be obtained as follows. Amplification is performed by the PCR method using as templates the entire or DNA portions encoding desired amino acid sequences (of DNA encoding the H-chain or the H-chain V-region of the above antibody, and DNA encoding the L-chain or the L-chain V-region), and using a primer pair that specifies both ends. Amplification is then further performed using DNA encoding a peptide linker portion and a primer pair that specify each end for ligation to the H-chain and L-chain.

Furthermore, once DNA encoding scFv is prepared, expression vectors containing the DNA, and hosts transformed with the expression vectors, can be obtained according to the standard method. In addition, by the use of the host, scFv can be obtained according to the standard method.

These antibody fragments can be produced by obtaining the genes thereof in a manner similar to the above method, and then causing the expression of the genes in a host. The "antibody" in the present invention encompasses such antibody fragments.

Anti-glypican antibodies bound to one of various molecules such as a labeling substance can be used as a modified antibody. The "antibody" in the present invention also encompasses these modified antibodies. Such a modified antibody can be obtained by chemically modifying the antibody obtained as above. Methods for antibody modification have been established in the art.

Furthermore, the antibody used in the pre sent invention may be a bispecific antibody. The bispecific antibody may have antigen-binding sites that recognize different epitopes on a GPC3 molecule. Alternatively, one antigen-binding site may recognize GPC3 and the other antigen-binding site may recognize a labeling substance or the like. A bispecific antibody can be prepared by binding H-L pairs of two types of antibodies, or by fusing hybridomas producing different monoclonal antibodies. Furthermore, it can al so be prepared by genetic engineering techniques.

Antibodies can be expressed from the antibody genes constructed as described above by a known method. In the case of mammalian cells, the antibodies can be expressed by operably linking a useful conventional promoter, the antibody gene to be expressed, and a polyA signal at the 3' downstream thereof. A promoter/enhancer includes, for example, a human cytomegalovirus immediate early promoter/enhancer.

Furthermore, examples of another promoter/enhancer that can be used in the present invention for antibody expression include a virus promoter/enhancer such as a retrovirus, a polyoma virus, an adenovirus or a simian virus 40 (SV40), or a promoter/enhancer derived from a mammalian cell such as human elongation factor 1a (HEF1a).

When a SV40 promoter/enhancer is used, antibodies can be readily expressed by the method of Mulligan et al (Nature (1979) 277, 108), and when a HEF1a promoter/enhancer is used, antibodies can be readily expressed by the method of Mizushima et al (Nucleic Acids Res. (1990) 18, 5322).

In the case of *Escherichia coli*, a useful conventional promoter, a signal sequence for antibody secretion and an antibody gene are operably linked, so that the gene can be expressed. A promoter includes lacz promoter and araB promoter. When the lacz promoter is used, the antibody gene can be expressed by the method of Ward et al (Nature (1098) 341, 544-546; FASEB J. (1992) 6, 2422-2427), or when the araB promoter is used, the antibody gene can be expressed by the method of Better et al (Science (1988) 240, 1041-1043).

As a signal sequence for the antibody secretion, a pelB signal sequence (Lei, S. P. et al J. Bacteriol. (1987) 169, 4379) may be used when the antibody is produced in the periplasm of *Escherichia coli*. After antibodies produced in the periplasm are isolated, the structure of the antibody is appropriately refolded and used.

A replication origin may be derived from SV40, a polyoma virus, an adenovirus, a bovine papilloma virus (BPV) or the like. Furthermore, to amplify the copy number of the gene in a host cell system, an expression vector can contain an aminoglycoside transferase (APH) gene, a thymidine kinase (TK) gene, an *Escherichia coli* xanthine guanine phosphoribosyltransferase (Ecogpt) gene, a dihydrofolate reductase (dhfr) gene or the like as a selection marker.

To produce the antibodies used in the present invention, any expression systems such as a eukaryotic cell system or a prokaryotic cell system can be used. Examples of eukaryotic cells include animal cells such as cells of established mammalian cell lines or insect cell lines, and filamentous fungous cells and yeast cells. Examples of prokaryotic cells include bacterial cells such as *Escherichia coli* cells.

Preferably, antibodies used in the present invention are expressed in mammalian cells such as CHO, COS, myeloma, BHK, Vero or HeLa cells.

Next, a transformed host cell is cultured in vitro or in vivo, so as to cause the host cell to produce the intended antibody. Host cells may be cultured according to a known method. For example, DMEM, MEM, RPMI1640, IMDM or the like can be used as a medium. A serum fluid such as fetal calf serum (FCS) can be used in combination.

The antibodies expressed and produced as described above can be isolated from the cells or host animals, and purified to homogeneity. Isolation and purification of the antibodies to be used in the present invention can be performed using affinity columns. An example of a protein A column is Hyper D, POROS, Sepharose F.F. (Pharmacia). Any other standard isolation and purification methods for proteins may be used. For example, a chromatography column other than the above affinity column, a filter, ultrafiltration, salting out, dialyses and the like may be appropriately selected and combined for use, so that antibodies can be isolated and purified (Antibodies A Laboratory Manual. Ed Harlow, David Lane, Cold Spring Harbor Laboratory, 1988).

2. Detection of GPC3

GPC3 to be detected in the present invention is not specifically limited, and may be full-length GPC3 or a fragment thereof. When a GPC3 fragment is detected, the fragment may be either an N-terminal or C-terminal fragment, and is preferably the N-terminal fragment. Alternatively, the GPC3 to be detected may be a GPC3 protein to which heparan sulfate or the like is attached, or a GPC3 core protein.

A detection method of GPC3 proteins contained in a test sample is not specifically limited. Preferably, GPC3 proteins are detected by an immunological method using anti-GPC3 antibodies. Examples of an immunological method include radioimmunoassay, enzyme immunoassay, fluoroimmunoassay, luminescence immunoassay, immunoprecipitation, immuno-nephelometry, Western blot, immunostaining and immunodiffusion techniques. A preferred detection method is enzyme immunoassay, and a particularly preferred is enzyme-linked immunosorbent assay (ELISA) (e.g., sandwich ELISA). The above immunological methods such as ELISA can be performed by a method known to a person skilled in the art.

An example of conventional detection methods using anti-GPC3 antibodies involves immobilizing anti-GPC3 antibodies on a carrier, adding a test sample to the carrier, incubating the carrier to bind GPC3 proteins to anti-GPC3 antibodies, washing, and then detecting GPC3 proteins bound to the support via anti-GPC3 antibodies to detect a GPC3 protein in a test sample.

Examples of carriers to be used in the present invention include insoluble carriers such as insoluble polysaccharides (e.g., agarose or cellulose), synthetic resins (e.g., a silicone resin, a polystyrene resin, a polyacrylamide resin, a nylon resin or a polycarbonate resin) and glass. These carriers can be used in the form of beads or plates. In the case of beads, a column or the like can be filled with beads. In the case of a plate, a multi-well plate (e.g., a 96-well multi-well plate), a biosensor chip or the like can be used. Anti-GPC3 antibodies can be bound to a carrier by any of the conventional methods such as chemical binding or physical adsorption. Most of the carriers that can be used herein may be commercially available.

The binding of anti-GPC3 antibodies with GPC3 proteins is generally performed in a buffer. A buffer includes, for example, a phosphate buffer, a Tris buffer, a citric acid buffer, a borate buffer, a carbonate buffer or the like. Incubation is performed under conditions that have already been often used, for example, 1 to 24 hours of incubation at 4° C. to room temperature. Washing after incubation can be performed with any solution which does not disturb the binding of GPC3 proteins with anti-GPC3 antibodies. For example, a buffer containing a surfactant such as Tween20 is used.

In the detection method of GPC3 proteins of the present invention, a control sample can also be set in addition to a test sample containing GPC3 proteins to be detected. Examples of a control sample include a negative control sample containing no GPC3 protein and a positive control sample containing GPC3 proteins. In this case, the results obtained from the test sample are compared with the result from the negative control sample containing no GPC3 protein and the result from the positive control sample containing GPC3 proteins, so that GPC3 proteins in a test sample can be detected. Moreover, a series of control samples are prepared to have serially varied concentrations, the detection results from each control sample are obtained as numerical values, and standard curves are then produced. Based on the standard curves, the GPC3 protein contained in the test sample can be quantitatively determined from the numerical values obtained from the test sample.

A preferred embodiment of the detection of a GPC3 protein bound to a carrier via an anti-GPC3 antibody is a detection method using an anti-GPC3 antibody labeled with a labeling substance.

For example, a test sample is allowed to come into contact with an anti-GPC3 antibody immobilized on a carrier. After washing, GPC3 protein is detected using a labeled antibody that specifically recognizes the GPC3 protein.

Anti-GPC3 antibodies can be labeled by a generally known method. A labeling substance known by a person skilled in the art, such as a fluorescent dye, an enzyme, a co-enzyme, a chemiluminescence substance or a radioactive substance can be used. Specific examples of a labeling substance include a radioisotope (e.g., $^{32}P$, $^{14}C$, $^{125}I$, $^{3}H$, and $^{131}$I), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase and biotin. When biotin is used as a labeling substance, it is preferable to further add avidin bound to an enzyme such as alkaline phosphatase, after the addition of biotin-labeled antibodies. For the binding of labeling substances with anti-GPC3 antibodies, any of the known methods such as a glutaraldehyde method, a maleimide method, a pyridyl disulfide method or a periodic acid method can be used.

Specifically, a solution containing an anti-GPC3 antibody is added to a carrier such as a plate to allow the anti-GPC3 antibody to be immobilized on the carrier. After the plate is washed, it is blocked with, for example, BSA, gelatin, albumin or the like to avoid nonspecific binding of proteins. After the plate is washed again, a test sample is added to the plate. After incubation, the plate is washed, and then a labeled anti-GPC3 antibody is added. After an appropriate incubation, the plate is washed, and then the labeled-anti-GPC3 antibody remaining on the plate is detected. Detection can be performed by a method known by a person skilled in the art. For example, in the case of labeling with a radioactive substance, the labeled antibody can be detected by liquid scintillation or an RIA method. In the case of labeling with an enzyme, a substrate is added, and the consequence of the enzymatic reaction of the substrate such as color development can be detected by a spectrophotometer. Specific examples of a substrate include 2,2-azinobis (3-ethylbenzthiazoline-6-sulfonate) diammonium salt (ABTS), 1,2-phenylenediamine (ortho-phenylenediamine) and 3,3',5,5'-tetramethylbenzidine (TME). In the case of labeling with a fluorescent substance, the labeled antibody can be detected by a fluorometer.

A particularly preferred embodiment of the detection method of a GPC3 protein of the present invention makes use of a biotin-labeled anti-GPC3 antibody and avidin.

Specifically, a solution containing an anti-GPC3 antibody is added to a carrier such as a plate to allow the anti-GPC3 antibody to be immobilized on the plate. The plate is washed and blocked with BSA or the like to avoid nonspecific binding of proteins. The plate is washed again, and then a test sample is added to the plate. After incubation, the plate is washed, and then a biotin-labeled anti-GPC3 antibody is added. After appropriate incubation, the plate is washed, and then avidin conjugated to an enzyme such as alkaline phosphatase or peroxidase is added. After incubation, the plate is washed, a substrate corresponding to the enzyme conjugated to avidin is added, and then GPC3 protein is detected using as an indicator an enzymatic change of the substrate.

Another embodiment of the detection method of a GPC3 protein of the present invention involves using a primary antibody that specifically recognizes a GPC3 protein, and a secondary antibody that specifically recognizes the primary antibody.

For example, a test sample is allowed to come into contact with an anti-GPC3 antibody immobilized on a support. After incubation and washing, GPC3 proteins bound after washing are detected using a primary anti-GPC3 antibody and a secondary antibody that specifically recognizes the primary antibody. In this case, the secondary antibody has been preferably labeled with a labeling substance.

Specifically, a solution containing an anti-GPC3 antibody is added to a carrier such as a plate to allow the anti-GPC3 antibody to be immobilized to the plate. The plate is washed and blocked with BSA or the like to avoid nonspecific binding of proteins. The plate is washed again, and then a test sample is added to the plate. After incubation and washing, a primary anti-GPC3 antibody is added. After appropriate incubation, the plate is washed. Subsequently, a secondary antibody that specifically recognizes the primary antibody is added. After appropriate incubation, the plate is washed, and then the secondary antibody remaining on the plate is detected. The secondary antibody can be detected by the above-described method.

Another embodiment of the detection method of a GPC3 protein of the present invention involves using agglutination reaction. In this method, GPC3 can be detected using carriers sensitized with an anti-GPC3 antibody. Any carrier may be used for sensitization of the antibody, as long as it is insoluble, causes no nonspecific reaction and is stable. For example, latex particles, bentonite, collodion, kaolin or immobilized sheep erythrocytes can be used. Latex particles are preferably used. Latex particles used in the invention include, for example, polystyrene latex particles, styrene-butadiene copolymer latex particles or polyvinyl toluene latex particles. Polystyrene latex particles are preferably used. The sensitized particles are mixed with a sample, and then the mixture was agitated for a given period of time to observe agglutination. The higher the concentration of GPC3 antibodies contained in the sample is, the larger the agglutination degree of the particles is observed. Thus, GPC3 can be detected by macroscopic observation of the agglutination. In addition, GPC3 can also be detected by measuring turbidity resulting from agglutination using a spectrophotometer or the like.

Another embodiment of the detection method of a GPC3 protein of the present invention involves a biosensor utilizing the surface plasmon resonance phenomenon. With a biosensor utilizing the surface plasmon resonance phenomenon, the protein-protein interaction can be observed in realtime in the form of surface plasmon resonance signals using only a trace amount of proteins without labeling. For example, through the use of a biosensor of BIAcore (Pharmacia) or the like, the binding of GPC3 proteins to anti-GPC3 antibodies can be detected. Specifically, a test sample is allowed to come into contact with a sensor chip, on which an anti-GPC3 antibody has been immobilized, and then the GPC3 protein bound to the anti-GPC3 antibody can be detected as a change in resonance signals.

The detection method of the present invention can also be automated using various automatic testing systems, so that a large number of samples can be tested at one time.

Another object of the present invention is to provide a diagnostic reagent or a kit for detecting GPC3 proteins in a test sample for cancer diagnosis. The diagnostic reagent or the kit of the invention contains at least an anti-GPC3 antibody. When the diagnostic reagent or the kit is based on the ELISA method, the reagent or the kit may contain a carrier for immobilization of the antibody, or the antibody may have been previously bound to the carrier. When the diagnostic reagent or the kit is based on the agglutination method using carriers such as latex, the reagent or the kit may contain carriers having an antibody adsorbed thereon. In addition, the kit may also appropriately contain a blocking solution, a reaction solution, a reaction stop solution, a reagent for treating a sample, or the like.

BRIEF DESCRIPTION OF DRAWINGS

FIG. 1 shows the results of expression analysis of GPC3 mRNA using Gene Chip. FIG. 1A shows the expression of GPC3, and FIG. 1B shows the expression of alpha-fetoprotein (AFP). NL, CH, LC, WD, MD and PD on the horizontal axis respectively indicate a normal liver, chronic hepatitis site, liver cirrhosis site, well-differentiated carcinoma, moderately-differentiated carcinoma and poorly-differentiated carcinoma.

FIG. 2 shows an image of CBB staining of purified heparan sulfate-attached GPC3 and GPC3 core proteins.

FIG. 8 shows combinations of anti-GPC3 antibodies in ELISA.

BEST MODE FOR CARRYING OUT THE INVENTION

Figure 3:
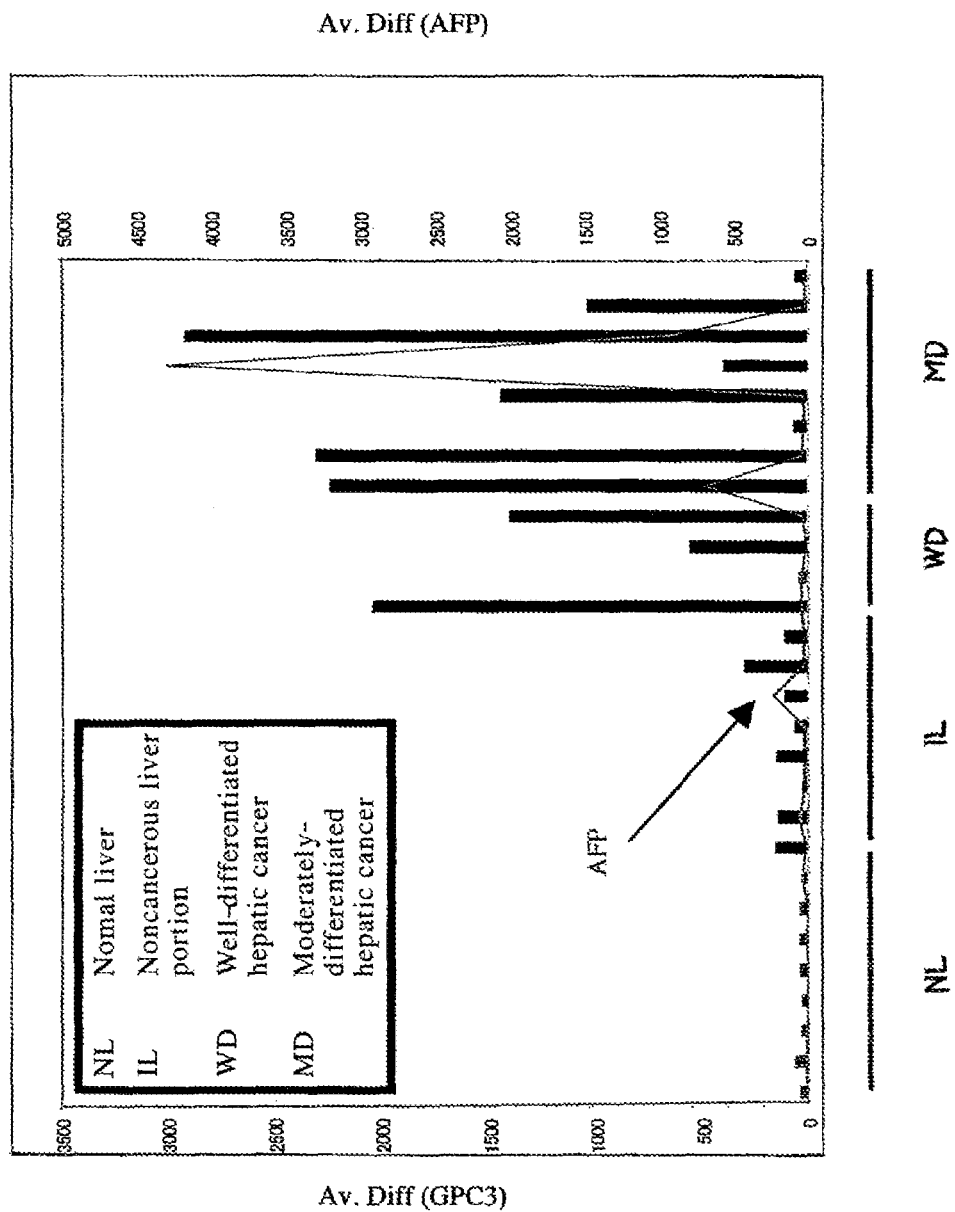
FIG. 3 shows the expression of a GPC3 gene in human hepatic cancer.

The present invention will be described in detail as follows. However, the present invention is not limited by these examples.

In the examples described in the specification of the present application, the following materials were used.

As expression vectors of a soluble GPC3 and a soluble GPC3 core protein, pCXND2 and pCXND3 that had been prepared by incorporating a DHFR gene and a neomycin-resistance gene into pCAGGS were used.

DXB11 cells used herein were purchased from ATCC. For culturing, 5% FBS (GIBCO BRL CAT#10099-141, LOT#A0275242)/Minimum Essential Medium Alpha Medium (α MEM(+))(GIBCO BRL CAT#12571-071)/1% Penicillin-Streptomycin (GIBCO BRL CAT#15140-122) was used. For the selection of DXB11 cells, 500 μg/mL Geneticin (GIBCO BRL CAT#10131-027)/5% FBS/a MEM without ribonucleosides and deoxyribonucleosides (GIBCO BRL CAT#12561-056) (a MEM(−))/PS was used alone or with supplemented with MTX at a final concentration of 25 nM.

HepG2 cells used herein were purchased from ATCC, and maintained in 10% FBS/Dulbecco's Modified Eagle Medium, DMEM) (GIBCO BRL CAT#11995-065)/PS.

Hybridomas were maintained in 10% FBS/RPMI1640/1× HAT media supplement (SIGMA CAT#H-0262)/0.5×BM-Condimed H1 Hybridoma cloning supplement (Roche CAT#1088947).

Example 1

Cloning and Expression Analysis of Human GPC (GPC3) cDNA

Cloning of the Full-Length cDNA Encoding Human Glypican 3 (Hereinafter Referred to as GPC3)

The full-length cDNA encoding human GPC3 was amplified by the PCR reaction using the 1st strand cDNA prepared by the standard method from colon cancer cell line Caco2 as a template, and an Advantage2 kit (CLONTECH, Cat. No8430-1). Specifically, 50 μl of a reaction solution containing 2 μl of the cDNA derived from Caco2, 1 μl of a sense primer (SEQ ID NO: 1), 1 μl of an antisense primer (SEQ ID NO: 2), 5 μl of Advantage2 10×PCR buffer, 8 μl of dNTP mix (1.25 mM), and 1.0 μl of Advantage polymerase mix was subjected to 35 cycles of a reaction cycle consisting of 94° C. for 1 minute, 63° C. for 30 seconds and 68° C. for 3 minutes. The amplified product (inserted in a TA vector pGEM-T easy using pGEM-T Easy Vector System I (Promega, Cat. No. A1360)) of the PCR was sequenced using an ABI3100 DNA sequencer to confirm that cDNA encoding full-length human GPC3 was isolated. The sequence represented by SEQ ID NO: 3 indicates the nucleotide sequence of the human GPC3 gene, and the sequence represented by SEQ ID NO: 4 indicates the amino acid sequence of the human GPC3 protein.

SEQ ID NO: 1: GATATC-ATGGCCGGGACCGTGCGCACCGCGT

SEQ ID NO: 2: GCTAGC-TCAGTGCACCAGGAAGAAGAAGCAC

Expression Analysis of Human GPC3 mRNA Using Gene Chip

The expression analysis of mRNA was performed using GeneChip™ UG95A Target (Affymetrix) for samples from 24 cases of hepatic cancer (well-differentiated carcinoma: WD; moderately-differentiated carcinoma: MD; poorly-differentiated carcinoma: PD), 16 cases of non hepatic cancer (chronic hepatitis portion: CH; liver cirrhosis portion: LC) and 8 cases of normal liver: NL. These samples were obtained from Graduate School of Medicine and Faculty of Medicine, the University of Tokyo and the Saitama Cancer Center under informed consent). Specifically, total RNA was prepared using ISOGEN (Nippon Gene Co., Ltd.) from each of the above tissues, and then 15 μg of each total RNA was used to perform gene expression analysis according to the Expression Analysis Technical Manual (Affymetrix).

As shown in FIG. 1, it was observed that the expression of the mRNA of the human GPC3 gene (Probe Set ID: 39350_at) in cancer tissues was higher than that of normal liver tissues in many cases regardless of the differentiation stages of hepatic cancer. Furthermore, the mRNA expression amount of the human GPC3 gene was compared with that of an alpha-fetoprotein (Probe Set ID: 40114_at) that is currently the most frequently employed as a diagnostic marker of hepatic cancer. As a result, sufficiently enhanced mRNA expression of GPC3 was observed even in well-differentiated carcinoma cases where almost no mRNA expression of the alpha-fetoprotein was observed, and it was revealed that the incidence of enhanced mRNA expression of GPC3 was higher than that of AFP. Based on the above results, it is thought that GPC3 detection is useful as an early diagnosis method of hepatic cancer.

Example 2

Preparation of Anti-GPC3 Antibodies Preparation of Soluble Human GPC3

A soluble GPC3 protein lacking the hydrophobic region on the C-terminal side was prepared as a material for preparing anti-GPC3 antibodies.

A soluble GPC3 cDNA expression plasmid DNA was constructed using a plasmid DNA containing full-length human GPC3 cDNA provided by the Research Center for Advanced Science and Technology, The University of Tokyo. PCR was performed using a downstream primer (5'-ATA GAA TTC CAC CAT GGC CGG GAC CGT GCG C-3' (SEQ ID NO: 5)) designed to eliminate the hydrophobic region (amino acid 564 to amino acid 580) on the C-terminal side and an upstream primer (5'-ATA GGA TCC CTT CAG CGG GGA ATG AAC GTT C-3' (SEQ ID NO: 6)) containing an EcoR I recognition sequence and a Kozak sequence. The thus obtained PCR fragment (1711 bp) was cloned into pCXND2-Flag. The thus prepared expression plasmid DNA was introduced into a CHO cell line DXB11. A CHO cell line highly expressing soluble GPC3 was obtained by selection using 500 µg/mL Geneticin.

Large-scale culture of the CHO cell line highly expressing soluble GPC3 was performed using a 1700 cm² roller bottle. The culture supernatant was collected and purified. The culture supernatant is applied to DEAE sepharose Fast Flow (Amersham CAT#17-0709-01). After washing, the product was eluted with a buffer containing 500 mM NaCl. Next, the product was affinity purified using Anti-Flag M2 agarose affinity gel (SIGMA CAT#A-2220), and eluted by 200 µg/mL FLAG peptide. After concentration using Centriprep-10 (Millipore CAT#4304), the FLAG peptide was removed by gel filtration using Superdex 200 HR 10/30 (Amersham CAT#17-1088-01). Finally, the protein was concentrated using a DEAE sepharose Fast Flow column, and eluted using a PBS (containing 500 mM NaCl) containing no Tween20 for buffer replacement.

Preparation of Soluble Human GPC3 Core Protein

A cDNA wherein the 495th Ser and 509th Ser were substituted with Ala was prepared by the assembly PCR method using the above wild type human GPC3 cDNA as a template. At this time, a primer was designed so that a His tag was added to the C-terminus. The thus obtained cDNA was cloned into a pCXND3 vector. The prepared expression plasmid DNA was introduced into a DXB11 cell line. A CHO cell line highly expressing soluble GPC3 core protein was obtained by selection using 500 µg/mL Geneticin.

Large-scale culture was performed using a 1700 cm² roller bottle. The culture supernatant was collected and purified. The culture supernatant was applied to Q sepharose Fast Flow (Amersham CAT#17-0510-01). After washing, the product was eluted using a phosphate buffer containing 500 mM NaCl. Next, the product was affinity purified using a Chelating sepharose Fast Flow (Amersham CAT#17-0575-01), and eluted with a gradient of 10 to 150 mM imidazole. Finally, the product was concentrated using a Q sepharose Fast Flow, and then eluted using a phosphate buffer containing 500 mM NaCl.

SDS polyacrylamide gel electrophoresis showed smear bands of 50 to 300 kDa and a band of approximately 40 kDa. FIG. 2 shows the result of electrophoresis. GPC3 is a proteoglycan having a heparan sulfate addition sequence on the C-terminus of 69 kDa. The smear bands were thought to be GPC3 modified with heparan sulfate. The amino acid sequencing revealed that the band of approximately 40 kDa contained a fragment of the N-terminal side of GPC3, suggesting that GPC3 had been subjected to some cleavage.

To eliminate antibodies against heparan sulfate in the following hybridoma screening, a soluble GPC3 core protein was prepared. Namely, two amino acid residues Ser 495 and Ser 509 serving as a heparin sulfate addition signal sequence were substituted with Ala. A CHO cell line highly expressing the protein was prepared as above, and then the culture supernatant was subjected to affinity purification utilizing the His-tag. SDS polyacrylamide gel electrophoresis showed three bands of 70 kDa, 40 kDa and 30 kDa. Amino acid sequencing revealed that the band of 30 kDa was a fragment on the C-terminal side of GPC3, showing that GPC3 had been subjected to some enzymatic cleavages between the 358th arginine and the 359th serine. The band of 30 kDa was not observed in the heparan sulfate-attached GPC3, possibly because heparan sulfate attached to GPC3 caused the band smear. The fact that GPC3 is enzymatically cleaved at a certain amino acid sequence is a new finding, and its biological significance has not yet been elucidated.

Based on this result, we have hypothesized that GPC3 on the membrane is cleaved also in hepatic cancer patients, and GPC3 of a soluble type is secreted in blood. The gene expression of GPC3 was found to be at a higher level in early hepatic cancer patients compared with that of AFP, which is a hepatic cancer tumor marker (FIG. 1). Hence, to investigate the ability of GPC3 as a potential new tumor marker with higher clinical utility than that of AFP, anti-GPC3 antibodies were prepared and sandwich ELISA systems were constructed as described in Example 2 and the subsequent examples.

Preparation of Anti-GPC3 Antibodies

Since human GPC3 and mouse GPC3 share high homology of 94% at the amino acid level, it was thought to be difficult to obtain anti-GPC3 antibodies when normal mice are immunized with human GPC3. Thus, MRL/lpr mice having autoimmune disease were used for immunization. 5 MRL/lpr mice (CRL) were immunized with soluble GPC3. The immunoprotein was prepared at 100 µg/mouse for initial immunization, and then emulsified using FCA (Freund's complete adjuvant (H37 Ra), Difco (3113-60), Becton Dickinson (cat#231131)). The emulsified product was administered subcutaneously. 2 weeks later, the protein was prepared at 50 µg/mouse, and then emulsified using FIA (Freund's incomplete adjuvant, Difco (0639-60), Becton Dickinson (cat#263910)). The emulsified product was administered subcutaneously. Subsequently, boosting immunization was performed at 1-week intervals 5 times in total. For the final immunization, the protein was diluted in PBS at 50 µg/mouse, and then administered via the caudal vein. After the saturation of serum antibody titer against GPC3 was confirmed by ELISA using an immunoplate coated with GPC3 core proteins, P3U1 mouse myeloma cells were mixed with mouse spleen cells to allow for cell fusion in the presence of PEG1500 (Roche Diagnostics, cat#783 641). The fused cells were inoculated on a 96-well culture plate, and selected using HAT media from the next day, and then the culture supernatant was screened by ELISA. Positive clones were monoclonalized by the limiting dilution method, followed by expansion culture, and then the culture supernatant was collected. Screening by ELISA was performed using the binding activity with GPC3 core proteins as an indicator, thereby obtaining 6 clones of anti-GPC3 antibodies having strong binding ability.

Antibodies were purified using Hi Trap ProteinG HP (Amersham CAT#17-0404-01). The hybridoma culture supernatant was directly applied to a column. After washing with a binding buffer (20 mM sodium phosphate (pH 7.0)), the antibodies were eluted with an elution buffer (0.1 M glycine-HCl (pH 2.7)). The eluate was collected in a tube containing a neutralization buffer (1 M Tris-HCl (pH 9.0)), so that the product was immediately neutralized. The antibody fraction was pooled and dialyzed against 0.05% Tween20/PBS overnight to replace the buffer. $NaN_3$ was added to the purified antibodies at 0.02%, and then the mixture was stored at 4° C.

Analysis of Anti-GPC3 Antibodies

Mouse IgG sandwich ELISA was performed using goat anti-mouse IgG (gamma) (ZYMED CAT#62-6600) and alkaline phosphatase-goat anti-mouse IgG (gamma) (ZYMED CAT#62-6622). The antibody concentration was quantified using a commercially available purified mouse IgG1 antibody (ZYMED CAT#02-6100) as a standard.

Isotyping of anti-GPC3 antibodies was performed using an ImmunoPure Monoclonal Antibody Isotyping Kit II (PIERCE CAT#37502) in accordance with the attached manual. The result of isotyping indicated that all the antibodies were of type IgG1.

Figure 4:
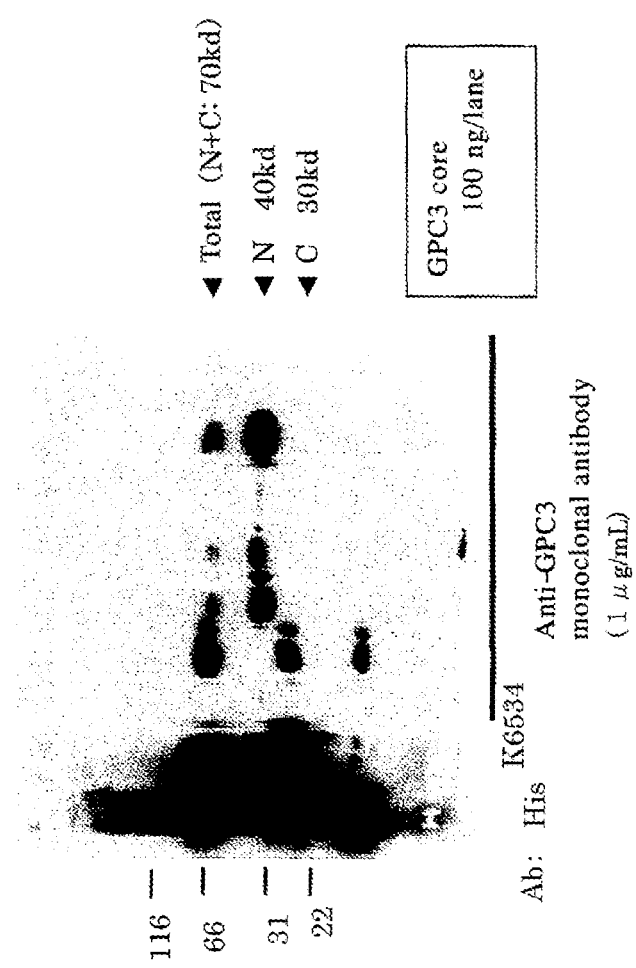
FIG. 4 shows the result of western blotting of a soluble core protein using an anti-GPC3 antibody.

Epitope classification of anti-GPC3 antibodies was performed by Western blotting using the GPC3 core proteins. The soluble GPC3 core proteins were applied to 10% SDS-PAGE mini (TEFCO CAT#01-075) at 100 ng/lane. After electrophoresis (60 V 30 min, 120 V 90 min), the proteins were transferred (15 V 60 min) to immobilon-P (Millipore CAT#IPVH R85 10) using a Trans-Blot SD Semi-Dry Electrophoretic Transfer Cell (BIO-RAD). The membrane was briefly washed with TBS-T (0.05% Tween20, TBS), followed by shaking for 1 hour (at room temperature) or overnight (at 4° C.) with TBS-T containing 5% skim milk. After approximately 10 minutes of shaking with TBS-T, each of the anti-GPC3 antibodies diluted to 0.1 to 10 μg/mL with TBS-T containing 1% skim milk was added, followed by 1 hour of shaking. After washing with TBS-T (10 minutes×3 times), HRP-anti-mouse IgG antibody (Amersham CAT#NA931) diluted to 1/1000 with 1% skim milk-containing TBS-T was added. After 1 hour of shaking, the membrane was washed with TBS-T (10 minutes×3 times), developed using ECL-Plus (Amersham RPN2132), and imaged on Hyperfilm ECL (Amersham CAT#RPN2103K). FIG. 4 shows the result of Western blot analysis. The antibodies were classified based on the fact that the antibodies reacting with a band of 40 kDa recognized the epitope on the N-terminus, and the antibodies reacting with a band of 30 kDa recognized the epitope on the C-terminus. M6B1, M18D4 and M19B11 antibodies, which recognize the N-terminal side, and M3C11, M13B3 and M3B8 antibodies, which recognize the C-terminal side, were obtained. As a result of analysis using BIACORE, the KD values of each of the antibodies were between 0.2 and 17.6 nM.

Example 3

Detection of Soluble GPC3 Mouse Xenograft Model 3,000,000 HepG2 human hepatic cancer cells were grafted subcutaneously to the abdominal portion of 6-week-old female SCID mice (Fox CHASE C.B-17/Icr-scid Jcl, CLEA Japan, Inc.) and nude mice (BALB/cA Jcl-nu, CLEA Japan, Inc.). 53 days later (when tumor mass had been sufficiently formed), the whole blood was collected via the posterior vena cava of HepG2-grafted SCID mice #1, 3 and 4. Plasma was prepared using a Nipro neotube (vacuum blood-collecting tube, NIPRO, NT-EA0205) in the presence of EDTA-2Na and aprotinin, and then stored at −20° C. by the day of measurement. In addition, the whole blood was collected from HepG2-grafted SCID mice #2 on day 62 after grafting of HepG2, and from HepG2-grafted nude mice #1 and 2 on day 66 after grafting through the posterior vena cava. As a control, plasma was also prepared in a similar procedure from normal SCID mice of the same age.

Sandwich ELISA

To detect soluble GPC3 in blood, a sandwich ELISA system of GPC3 was constructed. A 96-well plate was coated with M6B1, and GPC3 bound to M6B1 was detected by M18D4 antibody labeled with biotin. For color development, AMPAK (DAKO) was used to achieve high sensitivity detection.

A 96-well immunoplate was coated with the anti-GPC3 antibody diluted using a coating buffer (0.1 M $NaHCO_3$ (pH 9.6), 0.02% (w/v) $NaN_3$) at 10 μg/mL, followed by incubation overnight at 4° C. On the next day, the plate was washed 3 times with 300 μL/well washing buffer (0.05% (v/v) Tween20, PBS), and then 200 μL of dilution buffer (50 mM Tris-HCl (pH8.1), 1 mM $MgCl_2$, 150 mM NaCl, 0.05% (v/v) Tween20, 0.02% (w/v) $NaN_3$, 1% (w/v) BSA) was added for blocking. The plate was stand at room temperature for few hours or at 4° C. overnight, the mouse plasma or the culture supernatant appropriately diluted with a dilution buffer was added, and incubated at room temperature for 1 hour. After washing 3 times with 300 μL/well of RB, biotin-labeled anti-GPC3 antibodies diluted with a dilution buffer at 10 μg/mL were added, and incubated at room temperature for 1 hour. After washing 3 times with 300 μL/well of RB, AP-streptavidin (ZYMED) diluted to 1/1000 with a dilution buffer was added, and incubated at room temperature for 1 hour. After washing 5 times with 300 μL/well washing buffer, color development was performed using AMPAK (DAKO CAT#K6200) according to the attached protocols. Absorbance was then measured using a microplate reader.

Figure 5:
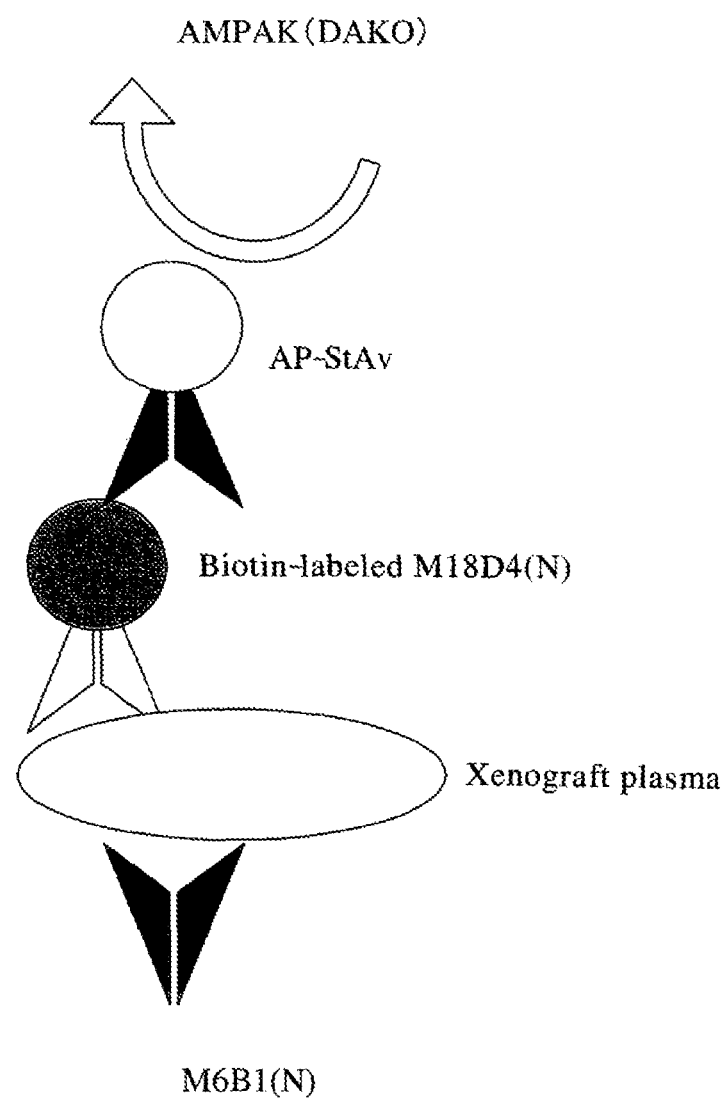
FIG. 5 shows the principles of sandwich ELISA using an anti-GPC3 antibody.

A Biotin Labeling Kit (CAT#1 418 165, Roche) was used for biotinylation of antibodies. The soluble GPC3 concentration in a sample was calculated using a GlaphPad PRISM spreadsheet program (GlaphPad software Inc. ver. 3.0). FIG. 5 shows the principles of the sandwich ELISA of this example.

Figure 6:
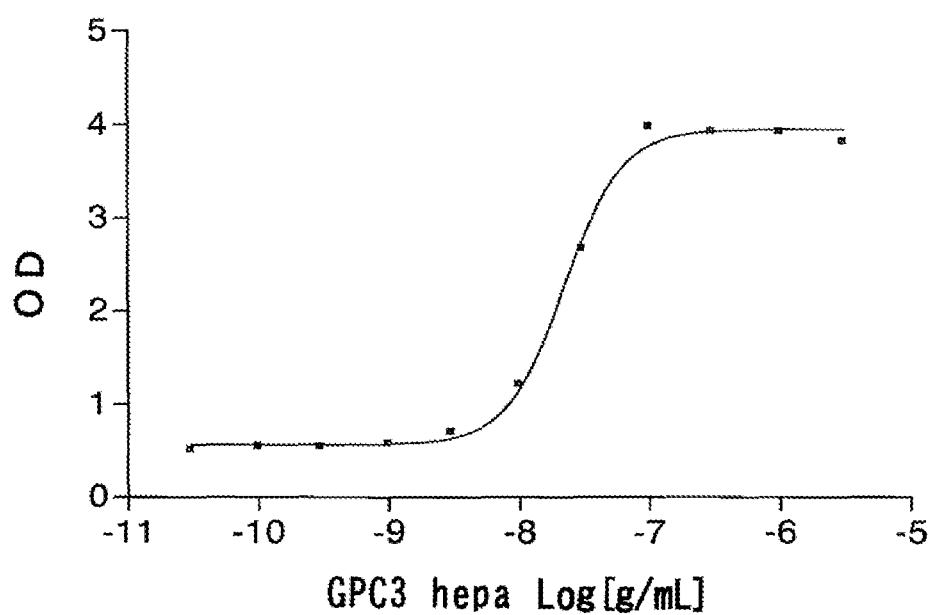
FIG. 6 shows the standard curve of GPC3 sandwich ELISA using M6B1 and M18D4.

A standard curve was prepared using purified soluble GPC3, so that a system having a detection limit of several ng/mL could be constructed. FIG. 6 shows the standard curve of the GPC3 sandwich ELISA using M6B1 and M18D4. Using this system, detection of GPC3 in the culture supernatant of the above HepG2 and the mouse sera to which HepG2 human hepatic cancer cells had been grafted was attempted. The soluble GPC3 was detected in the culture supernatant of HepG2 and in the sera of the mice to which HepG2 human hepatic cancer cells had been grafted, while the soluble GPC3 levels in the control medium and in control mouse sera were below the detection limit. When expressed in terms of the concentration of purified soluble GPC3, the concentration was 1.2 μg/mL in HepG2 culture supernatant, and 23 to 90 ng/mL in the mouse sera (Table 1).

limit in many mice. Accordingly, it was predicted that N-terminal fragment would be dominant in the secretory GPC3 discovered by the invention.

INDUSTRIAL APPLICABILITY

As shown in these examples, it was shown that GPC3 is highly expressed in hepatic cancer cells, and a portion of GPC3 may be present in blood in the form of a secretory protein. Since gene expression of GPC3 is observed in cancer tissues at a stage earlier than that of AFP, a hepatic cancer marker, detection of GPC3 is thought to be useful for cancer diagnosis. The expression of GPC3 was also found in cell lines of cancer other than hepatic cancer, such as lung cancer, colon cancer, cancer, prostate cancer, pancreatic

TABLE 1

Measurement of soluble GPC3 concentration in HepG2-grafted mouse plasma (ng/mL)

|  | Tumor volume (mm3) | M6B01(N)-M18D4(N) | M19B11(N)-M18D4(N) | M6B1(N)-BioM3C11(C) | M13B3(C)-BioM18D4(N) | M13B3(C)-BioM3B8(C) |
|---|---|---|---|---|---|---|
| HepG2 culture supernatant |  | 1190 | 1736 | 224 | 234 | <1 |
| HepG2-grafted SCID mouse #1 | 2022 | 65.4 | 76.9 | <10 | <10 | <10 |
| HepG2-grafted SCID mouse #2 | 1705 | 71.7 | 94.8 | <10 | <10 | <10 |
| HepG2-grafted SCID mouse #3 | 2257 | 90.3 | 113.9 | <10 | <10 | <10 |
| HepG2-grafted SCID mouse #4 | 2081 | 87.3 | 107.3 | <10 | 15.0 | <10 |
| HepG2-grafted nude mouse #1 | 1994 | 58.7 | 53.6 | 19.7 | 35.5 | 102.2 |
| HepG2-grafted nude mouse #2 | 190 & 549 | 22.9 | 33.6 | <10 | 11.5 | 40.6 |
| Normal SCID mouse #1 | 0 | <10 | <10 | <10 | <10 | <10 |
| Normal SCID mouse #2 | 0 | <10 | <10 | <10 | <10 | <10 |
| Normal SCID mouse #3 | 0 | <10 | <10 | <10 | <10 | <10 |

Structure of Secretory GPC3

Figure 7:
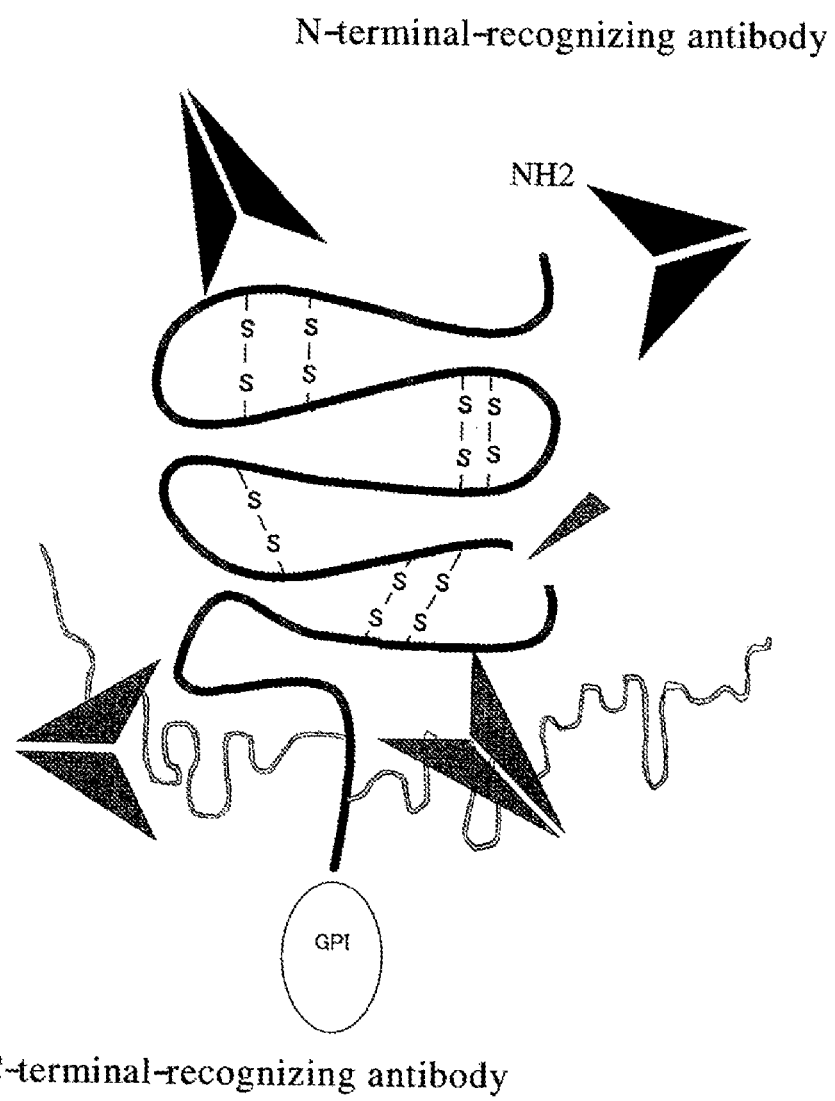
FIG. 7 is a schematic view showing the structure of GPC3.
Figure 9:
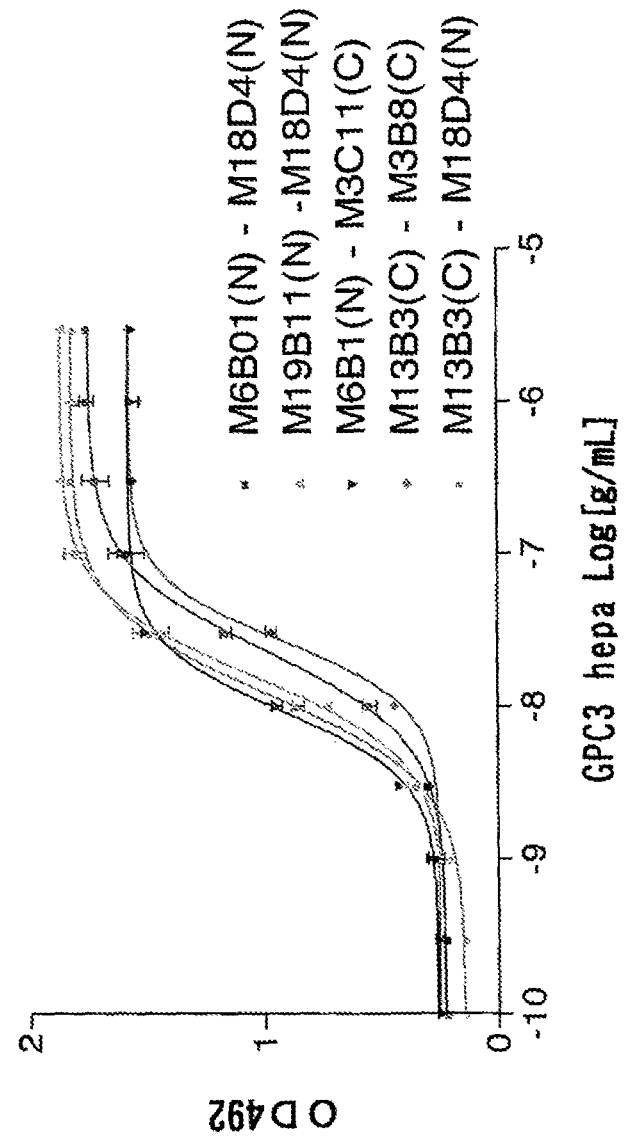
FIG. 9 shows standard curves of the GPC3 sandwich ELISA system using various combinations of anti-GPC3 antibodies.

It was investigated whether GPC3 was cleaved between the 358th arginine and the 359th serine and secreted as previously hypothesized. If secretory GPC3 is an N-terminal fragment, it may not be possible to detect this type of GPC3 with a sandwich ELISA using a combination of the antibody recognizing the N-terminus and the antibody recognizing the C-terminus. Using 3 types each of the antibodies recognizing the N-terminal fragment and the antibodies recognizing the C-terminal fragment, sandwich ELISA systems with various combinations of the antibodies were constructed. FIG. 7 shows the structure of secretory soluble GPC3, and FIG. 8 shows the combinations of antibodies. FIG. 9 shows the standard curves of the sandwich ELISA. Table 1 shows the measurement results. As shown in Table 1, secretory GPC3 was detected at high levels in the culture supernatant of HepG2, and in the sera of the mice to which HepG2 human hepatic cancer cells had been grafted using a combination of the antibodies, both of which recognize the N-terminal fragment. On the other hand, the detection results obtained with a system comprising antibodies recognizing the C-terminal fragment were below the detection limit in many mice.

cancer or lymphomas. Thus, GPC3 may have possible applications for diagnosis of cancers other than hepatic cancer.

Moreover, a possibility shown herein was that the N-terminal fragment cleaved between the 358th arginine and the 359th serine is dominantly present in the secretory GPC3. Accordingly, it is thought that the antibody recognizing the N-terminal fragment is useful as an antibody for diagnosis. Furthermore, if the antibody recognizing the C-terminal fragment is used as an antibody having ADCC activity and CDC activity for treating hepatic cancer, it may be able to efficiently reach hepatic cancer cells without being trapped by the secretory GPC3 present in blood.

All publications, patents and patent applications cited herein are incorporated herein by reference in their entirety. It is therefore to readily be understood by a person skilled in the art that numerous modifications and variations of the present invention are possible within the scope of the invention without departing from the technical idea and the scope of the invention as described in the appended claims. The present invention is intended to encompass such modifications and variations.

The invention claimed is:

1. A sandwich ELISA kit for diagnosing a possible presence of GPC3 protein expressing hepatic cancer in a human subject by detecting a soluble GPC3 protein level in a test sample obtained from the human subject, comprising two types of anti-GPC3 antibodies each recognizing the N-terminal peptide of GPC3, wherein the N-terminal peptide of GPC3 is a peptide fragment consisting of the amino acid sequence from the 1st amino acid to the 358th amino acid of SEQ ID NO: 4.

2. The kit of claim 1, wherein the test sample is selected from the group consisting of blood, serum and plasma.

3. The kit of claim 2, wherein the detected soluble GPC3 level in the test sample is greater than a control level of GPC3 in normal non-cancerous blood, serum or plasma, indicates the possible presence of GPC3 protein expressing hepatic cancer in the human subject.

4. The kit of claim 1, comprising an anti-GPC3 antibody immobilized on a carrier and an anti-GPC3 antibody labeled with a labeling substances.

5. The kit of claim 4, wherein the labeling substances are biotin.

* * * * *

SEQUENCE LISTING

<160> NUMBER OF SEQ ID NOS: 6

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 1
gatatcatgg ccgggaccgt gcgcaccgcg t                                    31

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
gctagctcag tgcaccagga agaagaagca c                                    31

<210> SEQ ID NO 3
<211> LENGTH: 2300
<212> TYPE: DNA
<213> ORGANISM: Homo sapiens
<220> FEATURE:
<221> NAME/KEY: CDS
<222> LOCATION: (109)..(1851)

<400> SEQUENCE: 3
cagcacgtct cttgctcctc agggccactg ccaggcttgc cgagtcctgg gactgctctc    60
gctccggctg ccactctccc gcgctctcct agctccctgc gaagcagg atg gcc ggg    117
                                                     Met Ala Gly
                                                       1 acc gtg cgc acc gcg tgc ttg gtg gtg gcg atg ctg ctc agc ttg gac    165
Thr Val Arg Thr Ala Cys Leu Val Val Ala Met Leu Leu Ser Leu Asp
      5                  10                  15 ttc ccg gga cag gcg cag ccc ccg ccg ccg ccg gac gcc acc tgt        213
Phe Pro Gly Gln Ala Gln Pro Pro Pro Pro Pro Asp Ala Thr Cys
 20                  25                  30                  35 cac caa gtc cgc tcc ttc ttc cag aga ctg cag ccc gga ctc aag tgg    261
His Gln Val Arg Ser Phe Phe Gln Arg Leu Gln Pro Gly Leu Lys Trp
             40                  45                  50 gtg cca gaa act ccc gtg cca gga tca gat ttg caa gta tgt ctc cct    309
Val Pro Glu Thr Pro Val Pro Gly Ser Asp Leu Gln Val Cys Leu Pro
         55                  60                  65 aag ggc cca aca tgc tgc tca aga aag atg gaa gaa aaa tac caa cta    357
Lys Gly Pro Thr Cys Cys Ser Arg Lys Met Glu Glu Lys Tyr Gln Leu
     70                  75                  80 aca gca cga ttg aac atg gaa cag ctg ctt cag tct gca agt atg gag    405
Thr Ala Arg Leu Asn Met Glu Gln Leu Leu Gln Ser Ala Ser Met Glu
 85                  90                  95 ctc aag ttc tta att att cag aat gct gcg gtt ttc caa gag gcc ttt    453
Leu Lys Phe Leu Ile Ile Gln Asn Ala Ala Val Phe Gln Glu Ala Phe
100                 105                 110                 115 gaa att gtt gtt cgc cat gcc aag aac tac acc aat gcc atg ttc aag    501
Glu Ile Val Val Arg His Ala Lys Asn Tyr Thr Asn Ala Met Phe Lys
             120                 125                 130 aac aac tac cca agc ctg act cca caa gct ttt gag ttt gtg ggt gaa    549
Asn Asn Tyr Pro Ser Leu Thr Pro Gln Ala Phe Glu Phe Val Gly Glu

```
                         135                 140                 145
ttt ttc aca gat gtg tct ctc tac atc ttg ggt tct gac atc aat gta         597
Phe Phe Thr Asp Val Ser Leu Tyr Ile Leu Gly Ser Asp Ile Asn Val
        150                 155                 160 gat gac atg gtc aat gaa ttg ttt gac agc ctg ttt cca gtc atc tat         645
Asp Asp Met Val Asn Glu Leu Phe Asp Ser Leu Phe Pro Val Ile Tyr
165                 170                 175 acc cag cta atg aac cca ggc ctg cct gat tca gcc ttg gac atc aat         693
Thr Gln Leu Met Asn Pro Gly Leu Pro Asp Ser Ala Leu Asp Ile Asn
180                 185                 190                 195 gag tgc ctc cga gga gca aga cgt gac ctg aaa gta ttt ggg aat ttc         741
Glu Cys Leu Arg Gly Ala Arg Arg Asp Leu Lys Val Phe Gly Asn Phe
                200                 205                 210 ccc aag ctt att atg acc cag gtt tcc aag tca ctg caa gtc act agg         789
Pro Lys Leu Ile Met Thr Gln Val Ser Lys Ser Leu Gln Val Thr Arg
        215                 220                 225 atc ttc ctt cag gct ctg aat ctt gga att gaa gtg atc aac aca act         837
Ile Phe Leu Gln Ala Leu Asn Leu Gly Ile Glu Val Ile Asn Thr Thr
                230                 235                 240 gat cac ctg aag ttc agt aag gac tgt ggc cga atg ctc acc aga atg         885
Asp His Leu Lys Phe Ser Lys Asp Cys Gly Arg Met Leu Thr Arg Met
        245                 250                 255 tgg tac tgc tct tac tgc cag gga ctg atg atg gtt aaa ccc tgt ggc         933
Trp Tyr Cys Ser Tyr Cys Gln Gly Leu Met Met Val Lys Pro Cys Gly
260                 265                 270                 275 ggt tac tgc aat gtg gtc atg caa ggc tgt atg gca ggt gtg gtg gag         981
Gly Tyr Cys Asn Val Val Met Gln Gly Cys Met Ala Gly Val Val Glu
                280                 285                 290 att gac aag tac tgg aga gaa tac att ctg tcc ctt gaa gaa ctt gtg        1029
Ile Asp Lys Tyr Trp Arg Glu Tyr Ile Leu Ser Leu Glu Glu Leu Val
                295                 300                 305 aat ggc atg tac aga atc tat gac atg gag aac gta ctg ctt ggt ctc        1077
Asn Gly Met Tyr Arg Ile Tyr Asp Met Glu Asn Val Leu Leu Gly Leu
        310                 315                 320 ttt tca aca atc cat gat tct atc cag tat gtc cag aag aat gca gga        1125
Phe Ser Thr Ile His Asp Ser Ile Gln Tyr Val Gln Lys Asn Ala Gly
325                 330                 335 aag ctg acc acc act att ggc aag tta tgt gcc cat tct caa caa cgc        1173
Lys Leu Thr Thr Thr Ile Gly Lys Leu Cys Ala His Ser Gln Gln Arg
340                 345                 350                 355 caa tat aga tct gct tat tat cct gaa gat ctc ttt att gac aag aaa        1221
Gln Tyr Arg Ser Ala Tyr Tyr Pro Glu Asp Leu Phe Ile Asp Lys Lys
                360                 365                 370 gta tta aaa gtt gct cat gta gaa cat gaa gaa acc tta tcc agc cga        1269
Val Leu Lys Val Ala His Val Glu His Glu Glu Thr Leu Ser Ser Arg
        375                 380                 385 aga agg gaa cta att cag aag ttg aag tct ttc atc agc ttc tat agt        1317
Arg Arg Glu Leu Ile Gln Lys Leu Lys Ser Phe Ile Ser Phe Tyr Ser
        390                 395                 400 gct ttg cct ggc tac atc tgc agc cat agc cct gtg gcg gaa aac gac        1365
Ala Leu Pro Gly Tyr Ile Cys Ser His Ser Pro Val Ala Glu Asn Asp
405                 410                 415 acc ctt tgc tgg aat gga caa gaa ctc gtg gag aga tac agc caa aag        1413
Thr Leu Cys Trp Asn Gly Gln Glu Leu Val Glu Arg Tyr Ser Gln Lys
420                 425                 430                 435 gca gca agg aat gga atg aaa aac cag ttc aat ctc cat gag ctg aaa        1461
Ala Ala Arg Asn Gly Met Lys Asn Gln Phe Asn Leu His Glu Leu Lys
                440                 445                 450 atg aag ggc cct gag cca gtg gtc agt caa att att gac aaa ctg aag        1509
```

```
Met Lys Gly Pro Glu Pro Val Val Ser Gln Ile Ile Asp Lys Leu Lys
              455                 460                 465
cac att aac cag ctc ctg aga acc atg tct atg ccc aaa ggt aga gtt    1557
His Ile Asn Gln Leu Leu Arg Thr Met Ser Met Pro Lys Gly Arg Val
            470                 475                 480
ctg gat aaa aac ctg gat gag gaa ggg ttt gaa agt gga gac tgc ggt    1605
Leu Asp Lys Asn Leu Asp Glu Glu Gly Phe Glu Ser Gly Asp Cys Gly
        485                 490                 495
gat gat gaa gat gag tgc att gga ggc tct ggt gat gga atg ata aaa    1653
Asp Asp Glu Asp Glu Cys Ile Gly Gly Ser Gly Asp Gly Met Ile Lys
500                 505                 510                 515
gtg aag aat cag ctc cgc ttc ctt gca gaa ctg gcc tat gat ctg gat    1701
Val Lys Asn Gln Leu Arg Phe Leu Ala Glu Leu Ala Tyr Asp Leu Asp
                520                 525                 530
gtg gat gat gcg cct gga aac agt cag cag gca act ccg aag gac aac    1749
Val Asp Asp Ala Pro Gly Asn Ser Gln Gln Ala Thr Pro Lys Asp Asn
            535                 540                 545
gag ata agc acc ttt cac aac ctc ggg aac gtt cat tcc ccg ctg aag    1797
Glu Ile Ser Thr Phe His Asn Leu Gly Asn Val His Ser Pro Leu Lys
        550                 555                 560
ctt ctc acc agc atg gcc atc tcg gtg gtg tgc ttc ttc ttc ctg gtg    1845
Leu Leu Thr Ser Met Ala Ile Ser Val Val Cys Phe Phe Phe Leu Val
565                 570                 575
cac tga ctgcctggtg cccagcacat gtgctgccct acagcaccct gtggtcttcc     1901
His
580 tcgataaagg gaaccacttt cttattttt tctatttttt tttttttgtt atcctgtata    1961
cctcctccag ccatgaagta gaggactaac catgtgttat gttttcgaaa atcaaatggt    2021
atcttttgga ggaagataca ttttagtggt agcatataga ttgtcctttt gcaaagaaag    2081
aaaaaaaacc atcaagttgt gccaaattat tctcctatgt ttggctgcta aacatggtt     2141
accatgtctt tctctctcac tccctcccct tctatcgttc tctctttgca tggatttctt    2201
tgaaaaaaaa taaattgctc aaataaaaaa aaaaaaaaaa aaaaaaaaaa aaaaaaaaaa    2261
aaaaaaaaaa aaaaaaaaaa aaaaaaaaaa aaaaaaaa                            2300

<210> SEQ ID NO 4
<211> LENGTH: 580
<212> TYPE: PRT
<213> ORGANISM: Homo sapiens

<400> SEQUENCE: 4

Met Ala Gly Thr Val Arg Thr Ala Cys Leu Val Val Ala Met Leu Leu
  1               5                  10                  15
Ser Leu Asp Phe Pro Gly Gln Ala Gln Pro Pro Pro Pro Pro Pro Asp
                 20                  25                  30
Ala Thr Cys His Gln Val Arg Ser Phe Phe Gln Arg Leu Gln Pro Gly
             35                  40                  45
Leu Lys Trp Val Pro Glu Thr Pro Val Pro Gly Ser Asp Leu Gln Val
         50                  55                  60
Cys Leu Pro Lys Gly Pro Thr Cys Cys Ser Arg Lys Met Glu Glu Lys
 65                  70                  75                  80
Tyr Gln Leu Thr Ala Arg Leu Asn Met Glu Gln Leu Leu Gln Ser Ala
                 85                  90                  95
Ser Met Glu Leu Lys Phe Leu Ile Ile Gln Asn Ala Ala Val Phe Gln
                100                 105                 110
Glu Ala Phe Glu Ile Val Val Arg His Ala Lys Asn Tyr Thr Asn Ala
```

```
            115                 120                 125
Met Phe Lys Asn Asn Tyr Pro Ser Leu Thr Pro Gln Ala Phe Glu Phe
130                 135                 140

Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
                165                 170                 175

Val Ile Tyr Thr Gln Leu Met Asn Pro Gly Leu Pro Asp Ser Ala Leu
            180                 185                 190

Asp Ile Asn Glu Cys Leu Arg Gly Ala Arg Arg Asp Leu Lys Val Phe
            195                 200                 205

Gly Asn Phe Pro Lys Leu Ile Met Thr Gln Val Ser Lys Ser Leu Gln
210                 215                 220

Val Thr Arg Ile Phe Leu Gln Ala Leu Asn Leu Gly Ile Glu Val Ile
225                 230                 235                 240

Asn Thr Thr Asp His Leu Lys Phe Ser Lys Asp Cys Gly Arg Met Leu
                245                 250                 255

Thr Arg Met Trp Tyr Cys Ser Tyr Cys Gln Gly Leu Met Met Val Lys
            260                 265                 270

Pro Cys Gly Gly Tyr Cys Asn Val Met Gln Gly Cys Met Ala Gly
            275                 280                 285

Val Val Glu Ile Asp Lys Tyr Trp Arg Glu Tyr Ile Leu Ser Leu Glu
290                 295                 300

Glu Leu Val Asn Gly Met Tyr Arg Ile Tyr Asp Met Glu Asn Val Leu
305                 310                 315                 320

Leu Gly Leu Phe Ser Thr Ile His Asp Ser Ile Gln Tyr Val Gln Lys
                325                 330                 335

Asn Ala Gly Lys Leu Thr Thr Thr Ile Gly Lys Leu Cys Ala His Ser
            340                 345                 350

Gln Gln Arg Gln Tyr Arg Ser Ala Tyr Tyr Pro Glu Asp Leu Phe Ile
            355                 360                 365

Asp Lys Lys Val Leu Lys Val Ala His Val Glu His Glu Thr Leu
370                 375                 380

Ser Ser Arg Arg Arg Glu Leu Ile Gln Lys Leu Lys Ser Phe Ile Ser
385                 390                 395                 400

Phe Tyr Ser Ala Leu Pro Gly Tyr Ile Cys Ser His Ser Pro Val Ala
                405                 410                 415

Glu Asn Asp Thr Leu Cys Trp Asn Gly Gln Glu Leu Val Glu Arg Tyr
            420                 425                 430

Ser Gln Lys Ala Ala Arg Asn Gly Met Lys Asn Gln Phe Asn Leu His
            435                 440                 445

Glu Leu Lys Met Lys Gly Pro Glu Pro Val Val Ser Gln Ile Ile Asp
            450                 455                 460

Lys Leu Lys His Ile Asn Gln Leu Leu Arg Thr Met Ser Met Pro Lys
465                 470                 475                 480

Gly Arg Val Leu Asp Lys Asn Leu Asp Glu Glu Gly Phe Glu Ser Gly
                485                 490                 495

Asp Cys Gly Asp Asp Glu Asp Glu Cys Ile Gly Gly Ser Gly Asp Gly
            500                 505                 510

Met Ile Lys Val Lys Asn Gln Leu Arg Phe Leu Ala Glu Leu Ala Tyr
            515                 520                 525

Asp Leu Asp Val Asp Asp Ala Pro Gly Asn Ser Gln Gln Ala Thr Pro
530                 535                 540
```

```
Lys Asp Asn Glu Ile Ser Thr Phe His Asn Leu Gly Asn Val His Ser
545                 550                 555                 560

Pro Leu Lys Leu Leu Thr Ser Met Ala Ile Ser Val Val Cys Phe Phe
                565                 570                 575

Phe Leu Val His
            580

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
atagaattcc accatggccg ggaccgtgcg c                                    31

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
ataggatccc ttcagcgggg aatgaacgtt c                                    31
```